US011511021B2

(12) United States Patent
Askem et al.

(10) Patent No.: US 11,511,021 B2
(45) Date of Patent: Nov. 29, 2022

(54) PROTECTION OF ELECTRONICS IN NEGATIVE PRESSURE WOUND THERAPY SYSTEMS

(71) Applicant: Smith & Nephew PLC, Watford (GB)

(72) Inventors: Ben Alan Askem, Brough (GB); Fernando Bettani, Milan (IT); Alberto Fasan, Milan (IT); Allan Kenneth Frazer Grugeon Hunt, Beverley (GB); Felix Clarence Quintanar, Hull (GB)

(73) Assignee: Smith & Nephew PLC, Watford (GB)

(*) Notice: Subject to any disclaimer, the term of this patent is extended or adjusted under 35 U.S.C. 154(b) by 915 days.

(21) Appl. No.: 16/334,124

(22) PCT Filed: Sep. 26, 2017

(86) PCT No.: PCT/US2017/053562

§ 371 (c)(1),
(2) Date: Mar. 18, 2019

(87) PCT Pub. No.: WO2018/064079

PCT Pub. Date: Apr. 5, 2018

(65) Prior Publication Data

US 2019/0231939 A1 Aug. 1, 2019

Related U.S. Application Data

(60) Provisional application No. 62/469,718, filed on Mar. 10, 2017, provisional application No. 62/401,727, filed on Sep. 29, 2016.

(51) Int. Cl.
*H02H 9/00* (2006.01)
*A61M 1/00* (2006.01)
(Continued)

(52) U.S. Cl.
CPC ............ *A61M 1/0023* (2013.01); *A61M 1/80* (2021.05); *A61M 1/90* (2021.05); *H05K 1/0257* (2013.01);
(Continued)

(58) Field of Classification Search
None
See application file for complete search history.

(56) References Cited

U.S. PATENT DOCUMENTS 7,557,302 B2 7/2009 Wang
8,366,692 B2 2/2013 Weston
(Continued)

FOREIGN PATENT DOCUMENTS

EP 0 369 374 5/1990
EP 1 418 798 5/2004
(Continued)

OTHER PUBLICATIONS

International Search Report and Written Opinion, re PCT Application No. PCT/US2017/053562, dated Jan. 8, 2018.
(Continued)

*Primary Examiner* — Stephen W Jackson
(74) *Attorney, Agent, or Firm* — Knobbe, Martens, Olson & Bear LLP

(57) ABSTRACT

Embodiments of negative pressure wound therapy systems and methods are disclosed. In one embodiment, an apparatus includes a housing, negative pressure source, circuit board, and one or more controllers. The circuit board can be supported by the housing and include a conductive pathway extending around at least part of a perimeter of a first side of the circuit board. The conductive pathway can be electrically coupled to an electrical ground for the circuit board.
(Continued)

The one or more controllers can be mounted on the circuit board and activate and deactivate the negative pressure source.

20 Claims, 24 Drawing Sheets

(51) Int. Cl.
*H05K 1/02* (2006.01)
*H05K 9/00* (2006.01)
*H05K 1/11* (2006.01)
*H05K 1/18* (2006.01)

(52) U.S. Cl.
CPC ........... *H05K 1/0259* (2013.01); *H05K 1/115* (2013.01); *H05K 1/181* (2013.01); *H05K 9/0067* (2013.01); *A61M 2205/0233* (2013.01); *A61M 2205/15* (2013.01); *A61M 2205/18* (2013.01); *A61M 2205/502* (2013.01); *A61M 2205/8206* (2013.01); *A61M 2209/088* (2013.01); *H05K 2201/093* (2013.01); *H05K 2201/09354* (2013.01); *H05K 2201/09618* (2013.01)

(56) References Cited

U.S. PATENT DOCUMENTS

| | | | |
|---|---|---|---|
| 10,086,117 B2 | 10/2018 | Locke et al. | |
| 2005/0088832 A1 | 4/2005 | Su et al. | |
| 2008/0275409 A1 | 11/2008 | Kane et al. | |
| 2010/0022990 A1 | 1/2010 | Karpowicz et al. | |
| 2014/0343518 A1* | 11/2014 | Riesinger .............. | A61M 1/964 604/319 |
| 2016/0136339 A1 | 5/2016 | Begin et al. | |
| 2018/0318476 A1 | 11/2018 | Askem et al. | |
| 2020/0022846 A1* | 1/2020 | Beadle ................ | A61F 13/0216 |

FOREIGN PATENT DOCUMENTS

| | | |
|---|---|---|
| EP | 3 060 034 | 8/2016 |
| JP | 2008153179 A | 7/2008 |
| WO | WO-2007013049 A1 | 2/2007 |
| WO | WO-2013007973 A2 | 1/2013 |
| WO | WO-2014140578 A1 | 9/2014 |
| WO | WO 2016/107775 | 7/2016 |
| WO | WO 2017/195038 | 11/2017 |
| WO | WO 2018/064079 | 4/2018 |

OTHER PUBLICATIONS

IEC, “Medical electrical equipment—Part 1: General requirements for basic safety and essential performance”, IEC 60601-1, Dec. 2005, in 786 pages (NPL document uploaded to EFS in two parts).
IEC, “Medical electrical equipment—Part 1: General requirements for basic safety and essential performance”, IEC 60601-1, Jul. 2012, in 236 pages.
International Preliminary Reporton Patentability for Application No. PCT/US2017/053562, dated Apr. 11, 2019, 8 pages.

* cited by examiner

PROTECTION OF ELECTRONICS IN NEGATIVE PRESSURE WOUND THERAPY SYSTEMS

CROSS-REFERENCE TO RELATED APPLICATIONS

This application is a U.S. national stage application of International Patent Application No. PCT/US2017/053562, filed Sep. 26, 2017, which claims the benefit of U.S. Provisional Application No. 62/401,727, filed Sep. 29, 2016, and U.S. Provisional Application No. 62/469,718, filed Mar. 10, 2017; the disclosures of which are hereby incorporated by reference in their entirety.

BACKGROUND

Embodiments of the present disclosure relate to methods and apparatuses for dressing and treating a wound with negative or reduced pressure therapy or topical negative pressure (TNP) therapy. In particular, but without limitation, embodiments disclosed herein relate to negative pressure therapy devices, methods for controlling the operation of TNP systems, and methods of using TNP systems.

BRIEF DESCRIPTION OF THE DRAWINGS

Features and advantages of the present disclosure will be apparent from the following detailed description, taken in conjunction with the accompanying drawings of which.

DETAILED DESCRIPTION

Figure 2:
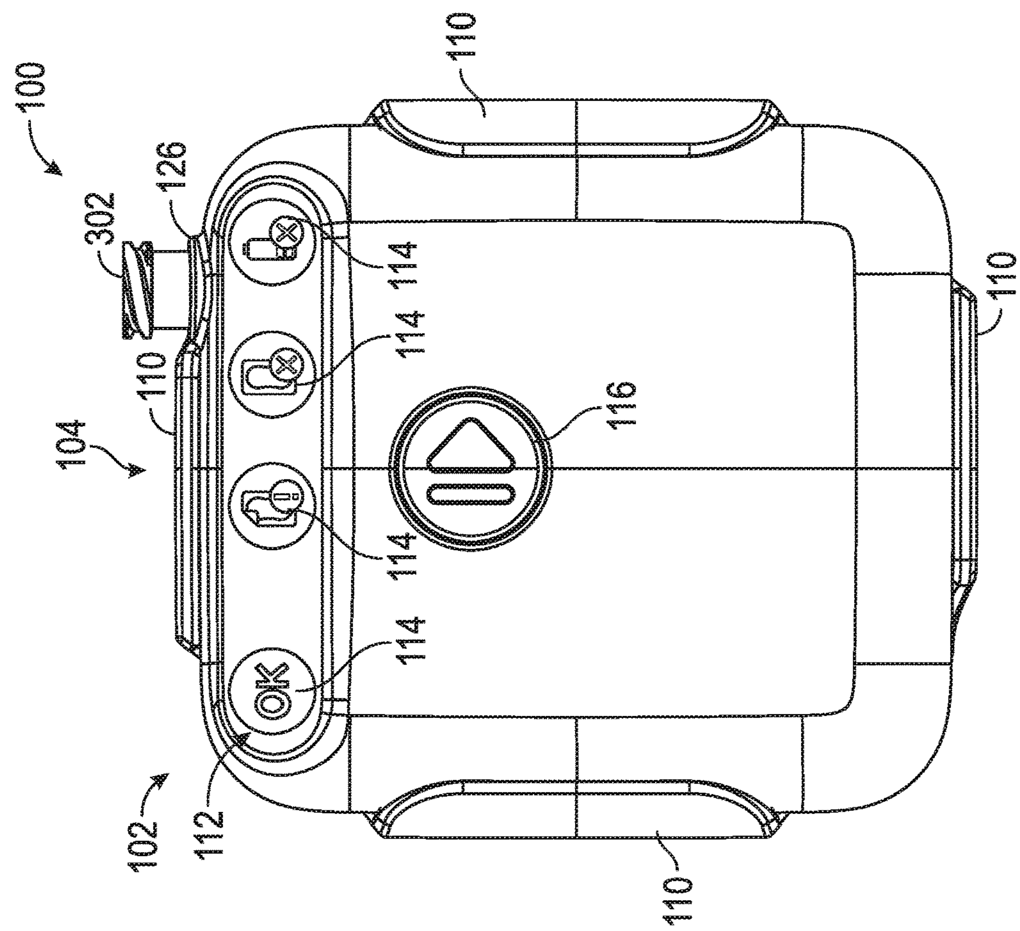
FIG. 2 is a front view of the pump system of FIG. 1.

The present disclosure relates to methods and apparatuses for dressing and treating a wound with reduced pressure therapy or topical negative pressure (TNP) therapy. The apparatuses and components comprising the wound overlay and packing materials, if any, are sometimes collectively referred to herein as wound dressings.

Many different types of wound dressings are known for aiding in the healing process of a human or animal. These different types of wound dressings include many different types of materials and layers, for example, gauze, pads, foam pads or multi-layer wound dressings. TNP therapy, sometimes referred to as vacuum assisted closure, negative pressure wound therapy, or reduced pressure wound therapy, can be a beneficial mechanism for improving the healing rate of a wound. Such therapy is applicable to a broad range of wounds such as incisional wounds, open wounds and abdominal wounds or the like.

TNP therapy can assist in the closure and healing of wounds by reducing tissue oedema, encouraging blood flow, stimulating the formation of granulation tissue, removing excess exudates, and reducing bacterial load and thus, infection to the wound. Furthermore, TNP therapy can permit less outside disturbance of the wound and promote more rapid healing.

As is used herein, reduced or negative pressure levels, such as −X mmHg, represent pressure levels that are below atmospheric pressure, which typically corresponds to 760 mmHg (or 1 atm, 29.93 inHg, 101.325 kPa, 14.696 psi, etc.). Accordingly, a negative pressure value of −X mmHg reflects pressure that is X mmHg below atmospheric pressure, such as a pressure of (760-X) mmHg. In addition, negative pressure that is “less” or “smaller” than −X mmHg corresponds to pressure that is closer to atmospheric pressure (for example, −40 mmHg is less than −60 mmHg). Negative pressure that is “more” or “greater” than −X mmHg corresponds to pressure that is further from atmospheric pressure (for example, −80 mmHg is more than −60 mmHg).

The operating negative pressure range can be between approximately −20 mmHg and approximately −200 mmHg, between approximately −50 mmHg and approximately −150 mmHg, between approximately −70 mmHg and −90 mmHg, any subrange within these ranges, or any other range as desired. In some instances, an operating negative pressure range of up to −70 mmHg, up to −80 mmHg, up to −90 mmHg, up to −100 mmHg, up to −110 mmHg, or up to any other pressure as desired can be used. For example, the pump system can maintain negative pressure wound therapy at −80 mmHg (nominal)+/−20 mmHg to a wound dressing or to a wound surface. Other details regarding the operation of the pump system are set forth in U.S. Publication Nos. 2011/0282309, 2013/0110058, and 2013/0331823 as well as International Patent Publication No. 2013/171585, and all embodiments, configurations, details, and illustrations of these publications are hereby incorporated by reference in their entireties.

Any of the embodiments disclosed herein can include a pump with or without a dressing kit. However, the pump systems and embodiments of the present disclosure are not limited to use with a wound dressing or for wound therapy. Any of the pump embodiments disclosed herein can be used independently of the wound dressing components disclosed herein. Further, any of the embodiments disclosed herein can be used, or can be adapted for use, for other purposes outside of negative pressure wound therapy. As such, any of the embodiments disclosed herein can be used, or can be adapted for use in systems for moving fluids (gaseous or liquid). Any of the embodiments disclosed herein can be used on an exuding wound. For instance, the pump or kit can be used on wounds where the level of exudate is low (for example, 0.6 g (nominal) of liquid exudate/cm2 of wound area per 24 hours), or on wounds where the level of exudate is moderate (for example, 1.1 g (nominal) of liquid exudate/cm2 of wound area per 24 hours). Exudate from the wound can be managed by the wound dressings disclosed herein through a combination of absorption in the wound dressing and an evaporation of moisture through the wound dressing. In embodiments where evaporation of exudate moisture through the wound dressing may be intended, occlusive materials positioned over the wound dressing area can impair evaporation.

Overview

Pump systems for performing TNP therapy can include one or more features that improve the tolerance of the pump system to environmental conditions, such as electromagnetic radiation or electrostatic discharge (ESD). The improved tolerance of the TNP apparatus can, for example, enable the TNP apparatus to function despite non-ideal environmental conditions or function more safely in the presence of certain environmental conditions.

Reduced Pressure Therapy Systems

The pump system embodiments described herein can have a compact, small size. In some implementations disclosed herein, a pump assembly of the pump system can have a diameter (for example, equivalent diameter) or lateral size between 15 mm and 35 mm, less than 15 mm, less than 25 mm, less than 35 mm, or less than 50 mm. For example, the pump system can have a diameter or lateral size of 10 mm, 23 mm, or 40 mm, or can have a diameter or lateral size in the range of approximately 26 mm to approximately 27 mm, between approximately 22 mm or smaller and approximately 28 mm. In some embodiments disclosed herein, the pump assembly can have a thickness or height of approximately 8 mm, between approximately 6 mm and approximately 10 mm, or a thickness or height of less than 20 mm. For example, the thickness or height of the pump assembly can be 5 mm, 12 mm, or 20 mm, and the pump assembly can have a volume of approximately 6.2 cubic centimeters, between approximately 5.0 cubic centimeters or less to approximately 7.0 cubic centimeters, or a volume of less than 10.0 cubic centimeters. For example, the volume of the pump assembly can be 4.0 cubic centimeters, 6.0 cubic centimeters, or 8.0 cubic centimeters. In some embodiments, the housing of can have a lateral size of approximately 60.0 mm, between approximately 40.0 mm and approximately 80.0 mm, or a lateral size of less than 90 mm, and a height of approximately 15.0 mm, between approximately 10.0 mm and approximately 20.0 mm, or a height of less than 30 mm. For example, the housing can have a Length×Width×Height dimension of 72 mm×66 mm×21 mm, approximately 72 mm×66 mm×21 mm, 70-73 mm×64-67 mm×20-22 mm, or a Length×Width×Height dimension of less than 90 mm×less than 90 mm×less than 30 mm. In yet other examples, the Length×Width×Height dimension of the housing can be 68 mm×62 mm×18 mm, 65 mm×78 mm×21 mm, 65 mm×79 mm×21 mm, or 80 mm×74 mm×25 mm. In some embodiments, the pump system can have a mass of 150 grams, approximately 150 grams, between 100-150 grams, or a mass of less than 200 grams, or a mass of less than 300 grams. For example, the mass of the pump system can be 90 grams, 125 grams, 150 grams, or 220 grams. The pump system can be any miniaturized size and have any mass and volume that is manufacturable, and the overall power output and efficiency meet the needed requirements for the desired application, within or outside of wound therapy. As used herein, efficiency can be defined as (fluid power out)/(electrical power in).

The pump system can be produced for a low cost and can operate at high efficiencies, making it beneficial for portable, disposable, or single use applications. This pump can optionally be used in an ultra-portable single-use negative-pressure wound therapy device. In some embodiments, the pump system can run for 10 days on a small primary cell without the need for battery replacement or recharging. For instance, the pump system can run up to 10 days on a 3V, 2000 mAh cell (for example, with the pump working for about 20% of the time) and can be powered by two 1.5 volt, 2500-3000 mAh batteries connected in series. In some implementations, the pump system can run for a week on a small primary cell such as one or more batteries having a total capacity of 3000 mAh at 3V without the need for battery replacement or recharging. Additionally, the pump system can be subjected to X-ray scans during its use without interfering with its function. In some embodiments, the pump system can be worn during computed tomography (CT) scans, computerized axial tomography (CAT) scans, and the like.

Figure 1:
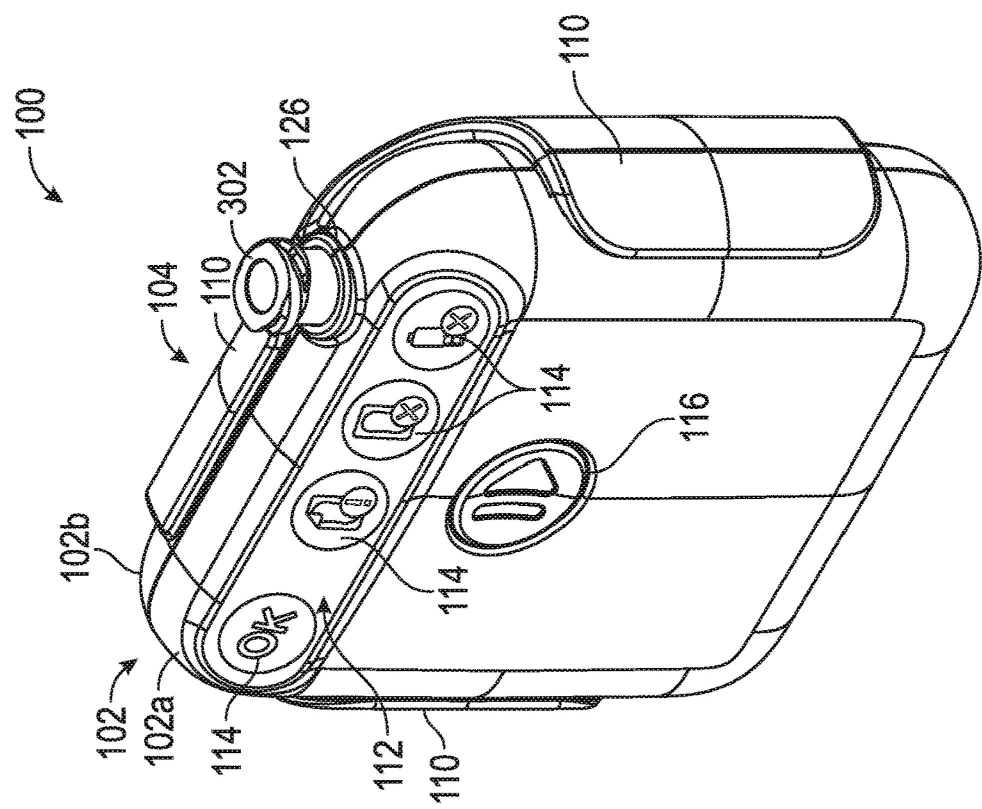
FIG. 1 is a front perspective view a pump system having an outer housing with an optional mounting component attached thereto according to some embodiments.
Figure 4:
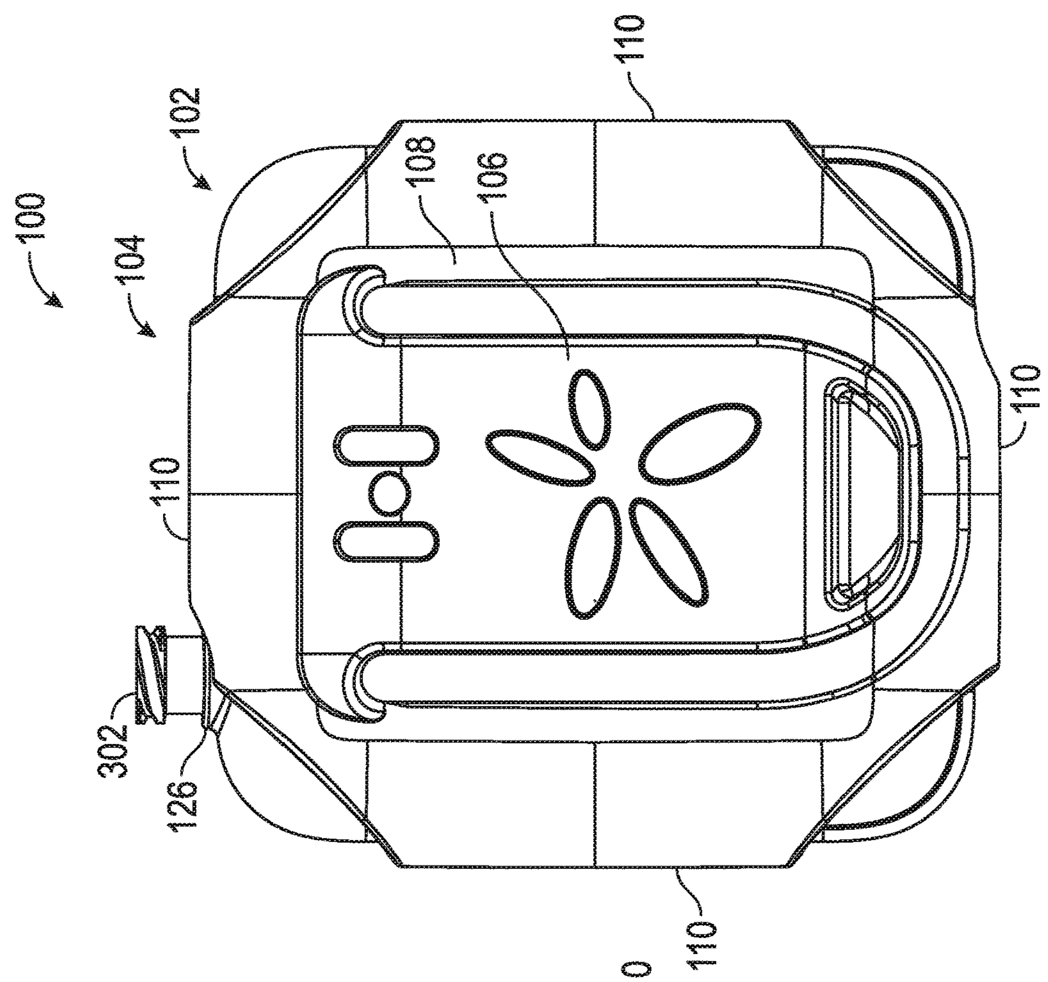
FIG. 4 is a rear view of the pump system of FIG. 1.
Figure 3:
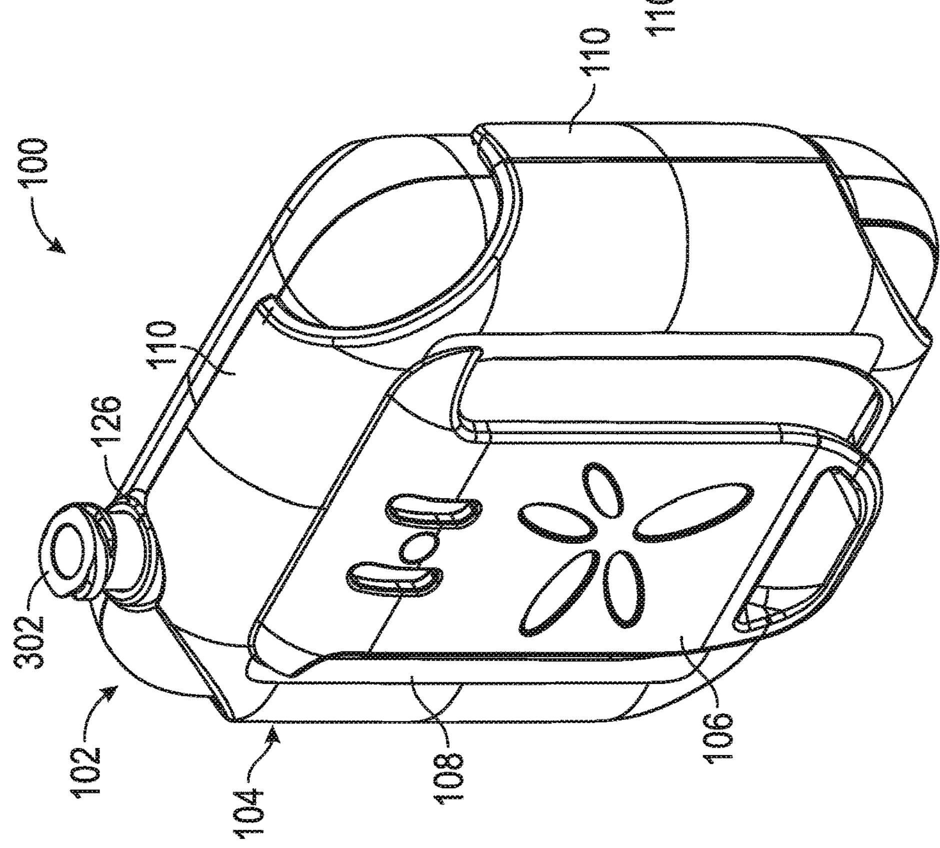
FIG. 3 is a rear perspective view of the pump system of FIG. 1.
Figure 6:
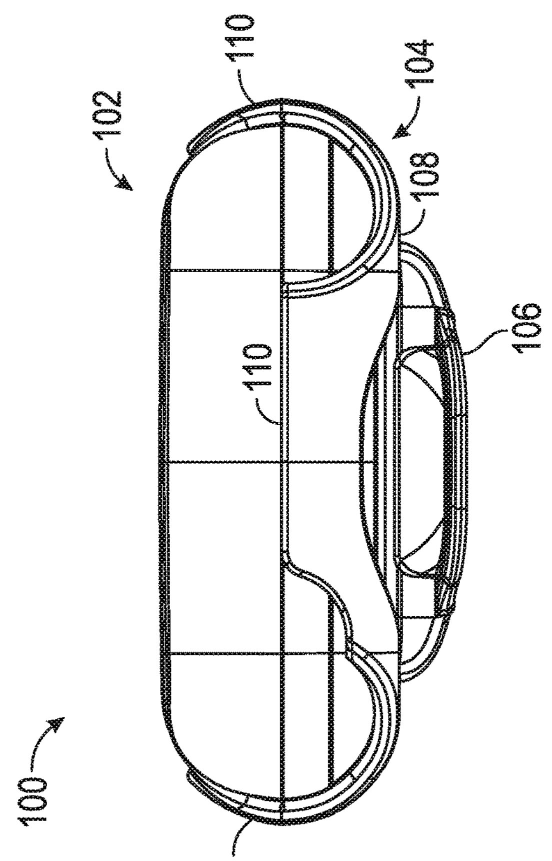
FIG. 6 is a bottom view of the pump system of FIG. 1.
Figure 5:
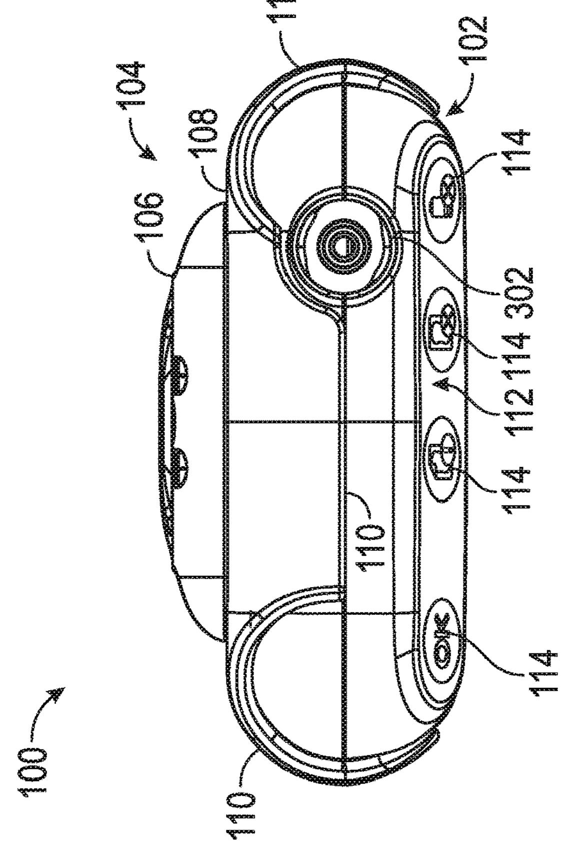
FIG. 5 is a top view of the pump system of FIG. 1.
Figure 8:
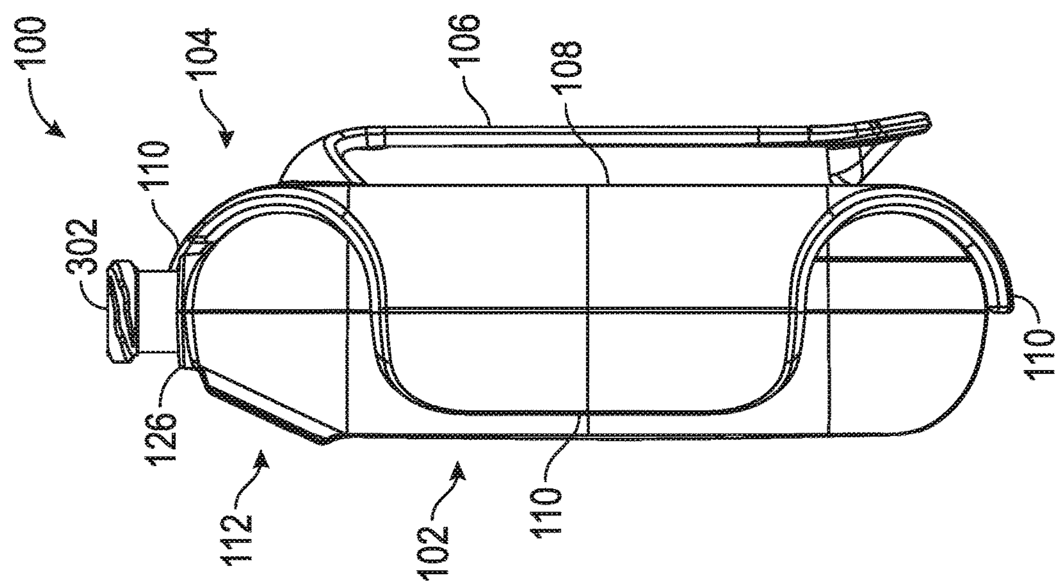
FIG. 8 is a left-side view of the pump system of FIG. 1.
Figure 7:
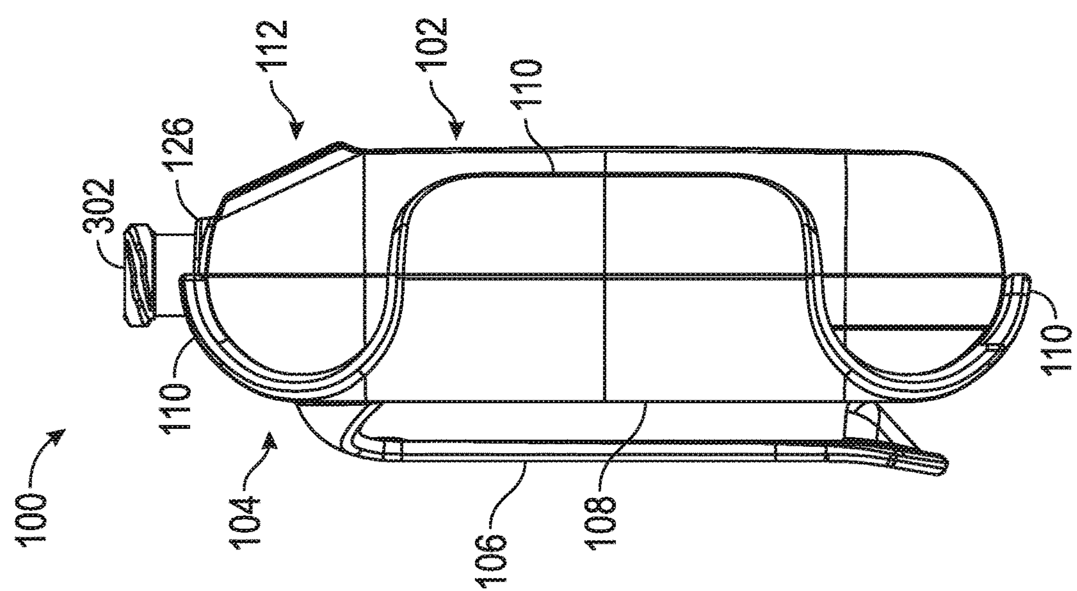
FIG. 7 is a right-side view of the pump system of FIG. 1.

FIGS. 1-8 illustrate multiple views of a pump system 100 having an outer housing 102 and a mounting component 104 according to some embodiments. As shown in FIGS. 1-8, the pump system 100 can include an outer housing 102 for containing or supporting components of the pump system 100. The outer housing 102 can be formed from one or more portions, such as a front portion **102*a* and a rear portion 102*b* as shown in FIG. 1, which can be removably attached to form the outer housing 102**.

The pump system 100 can optionally include a mounting component 104 which can be designed to allow the pump system 100 to be mounted on another object such as, but not limited to, a user's person. In some embodiments, the mounting component 104 can include a dip 106 (as shown in FIGS. 3-8) designed to retain the mounting component 104 on a user's outerwear, such as on a user's pocket, a pouch, a belt, a flap, or otherwise. The dip 106 can be integrally formed with the base 108 of the mounting component 104 such that the dip 106 can provide a clamping force via resiliency of the material used to form the dip 106. In some embodiments, the dip 106 can be a separate component from the base 108 and can include a biasing component, such as a coil spring, bent spring or the like, to provide a clamping force to retain the clip 106 on the user's person. In some embodiments, the clamping force can be low enough that a user can open the housing from the clamped position, but strong enough so that it will remain clamped about the pocket, flap, or other material.

The mounting component 104 can be removably attached to the outer housing 102 such that the pump system 100 can be used with or without the mounting component 104. For example, FIGS. 1-8 illustrate the pump system 100 with the optional mounting component 104. This can beneficially give the user the option to reduce the overall form factor of the pump system 100 should the user decide to forego use of the optional mounting component 104. Moreover, this can advantageously allow a user to more easily replace one mounting component with another mounting component should the user decide to do so. As shown in the illustrated embodiment, the mounting component 104 can include one or more retention features, such as clasps 110 extending from the periphery of the base 108, to retain the mounting component 104 on portions of the outer housing 102. In the illustrated embodiment, the mounting component 104 can be retained on the pump system 100 in a snap fit manner via use of the clasps 110. In some embodiments, the retention features can be mechanical fasteners such as screws, nuts, bolts, snap-fit connectors, or the like.

With continued reference to the pump system 100 of FIGS. 1-8, the outer housing 102 can include a display 112 which can be designed to provide a user with information (for example, information regarding an operational status of the pump system 100). In some embodiments, the display 112 can include one or more indicators, such as icons 114, which can alert the user to one or more operating or failure conditions of the pump system 100. For example, the indicators can include icons for alerting the user to normal or proper operating conditions, pump failure, power failure, the condition or voltage level of the batteries, the condition or capacity of a wound dressing, detection of a leak within the wound dressing or fluid flow pathway between the wound dressing and the pump assembly, suction blockage, or any other similar or suitable conditions or combinations thereof. An example set of icons 114 is illustrated in FIG. 1 which, from left to right, can include an "OK" indicator which can indicate normal operation of the pump system 100, a "leak" indicator which can indicate the existence of a leak in the pump system 100 or components attached thereto, a "dressing full" indicator which can indicate that a wound dressing is at or near capacity, and a "battery critical" indicator which can indicate that the battery is at or near a critical level. The icons 114 can have a green or orange color, or can be illuminated with a green or orange light (for example, colored LEDs).

In the illustrated embodiment, one or more icons 114 can be printed directly on the display 112 of the outer housing 102. In some embodiments, one or more of the icons 114 can be provided on a label attached to a portion of the outer housing 102. One or more of the icons 114 can be illuminated when the status corresponding to that icon exists in the system. As will be discussed in further detail below, one or more illumination components, such as LEDs, can be positioned within the outer housing 102 to illuminate the icons 114. To enhance illumination of the icons using an illumination component within the outer housing 102, portions of the outer housing 102 proximate or underlying one or more of the icons 114 can be reduced in thickness to increase the translucency of the outer housing 102 proximate or underlying the icons 114. In some embodiments, portions of the outer housing 102 proximate or underlying one or more of the icons 114 can be made from a transparent material. For example, in some embodiments, the display 112 of the outer housing 102 can comprise an illumination panel that is thinned or made of transparent or translucent material. Thinning portions of the outer housing 102 or making portions of the outer housing 102 from a transparent or translucent material can allow light from the illumination components to pass through the housing 102 and illuminate the icons 114. Advantageously, as no openings are formed in the outer housing 102 to provide illumination for the one or more icons 114 with a thinner or transparent or translucent housing, the potential for leakage around the icons 114 is eliminated or at least significantly reduced.

With continued reference to the pump system 100 illustrated in FIGS. 1-8, the pump system 100 can include one or more user input features, such as button 116, designed to receive an input from the user for controlling the operation of the pump system 100. In the embodiment shown, a single button is present which can be used to activate and deactivate the pump system 100 or control other operating parameters of the pump system 100. For example, in some embodiments, the button 116 can be used to activate the pump system 100, pause the pump system 100, clear indicators such as icons 114, or be used for any other suitable purpose for controlling an operation of the pump system 100 (for example, by sequentially pushing on the button 116). The button can be a push style button that can be positioned on an outside, front surface of the housing. In other embodiments, multiple input features (for example, multiple buttons) can be provided on the pump system 100.

In some embodiments, the button 116 can be designed to eliminate or at least reduce the potential for leakage around the button 116. In some embodiments, a peripheral portion of the button 116 can be placed in an interference fit with a surrounding lip of the outer housing 102. In some embodiments, the entirety or portions of the button 116 can be formed of a deformable material capable of forming a relatively hermetic seal when abutted against a surface, such as rubber, silicon, or any other suitable material.

Figure 16A:
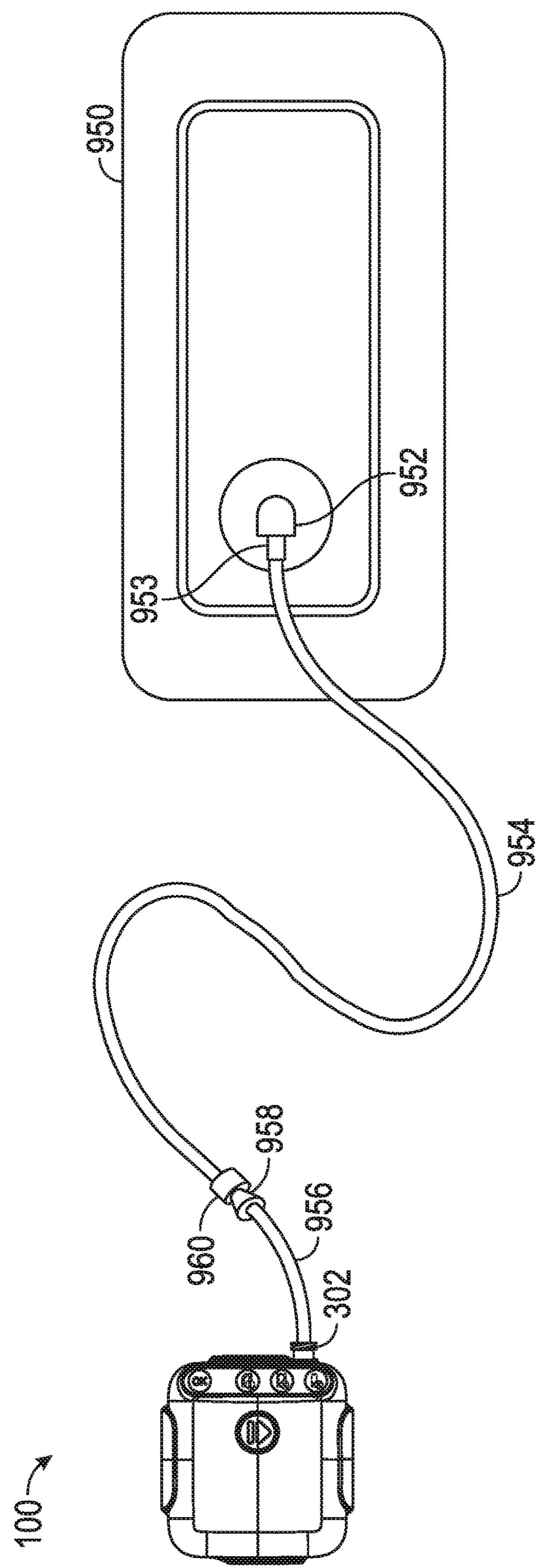
FIG. 16A is a top view of a pump system attached to a wound dressing according to some embodiments.
Figure 16B:
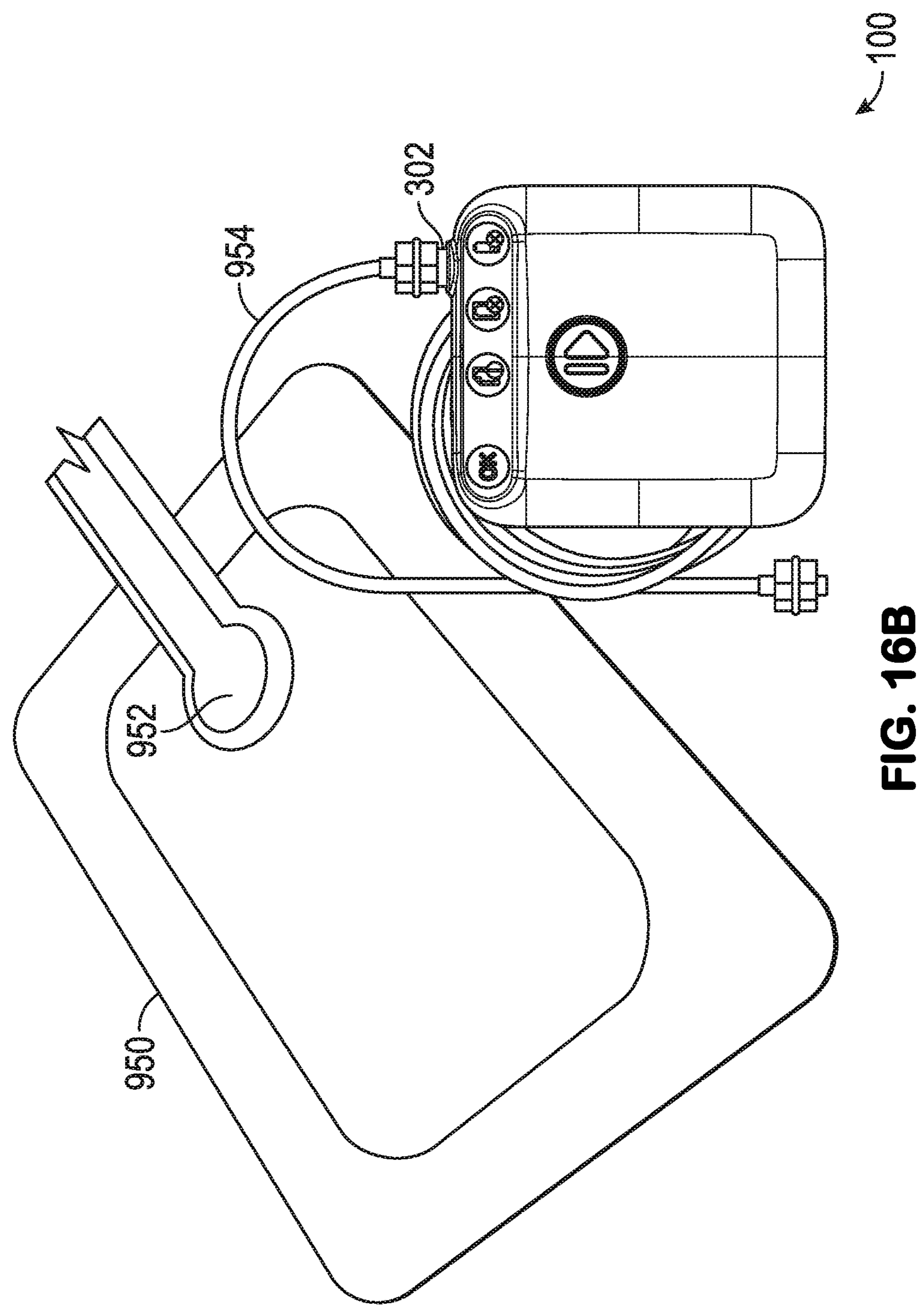
FIG. 16B is a view of a pump system configured to be attached to a wound dressing according to some embodiments.

In some embodiments, the pump system 100 can include a connector 302 for connecting a tube or conduit to the pump system 100. For example, as shown in FIGS. 16A and 16B, the connector 302 can be used to connect the pump system 100 to a dressing 950. As shown in the illustrated embodiment, the wound dressing 950 can include a port 952 for receiving an end of the conduit 954. In some embodiments, the port 952 can include a connector portion 953 for receiving the conduit 954. In some embodiments, the conduit 954 can be connected directly to the connector 302 of the pump system 100. In some embodiments, such as that shown in FIG. 16A, an intermediate conduit 956 can be used and attached to conduit 954 via a connector, such as a quick release connector 958, 960.

In some embodiments, the pump system can be configured to operate in a canisterless system, in which the wound dressing, such as wound dressing 950, retains exudate aspirated from the wound. Such a dressing can include a filter, such as a hydrophobic filter, that prevents passage of liquids downstream of the wound dressing (toward the pump system). In other embodiments, the pump system can be configured to operate in a system having a canister for storing at least part of exudate aspirated from the wound. Such canister can include a filter, such as a hydrophobic filter, that prevents passage of liquids downstream of the wound dressing (toward the pump system). In yet other embodiments, both the wound dressing and the canister can include filters that prevent passage of liquids downstream of the wound dressing and the canister.

Figure 10:
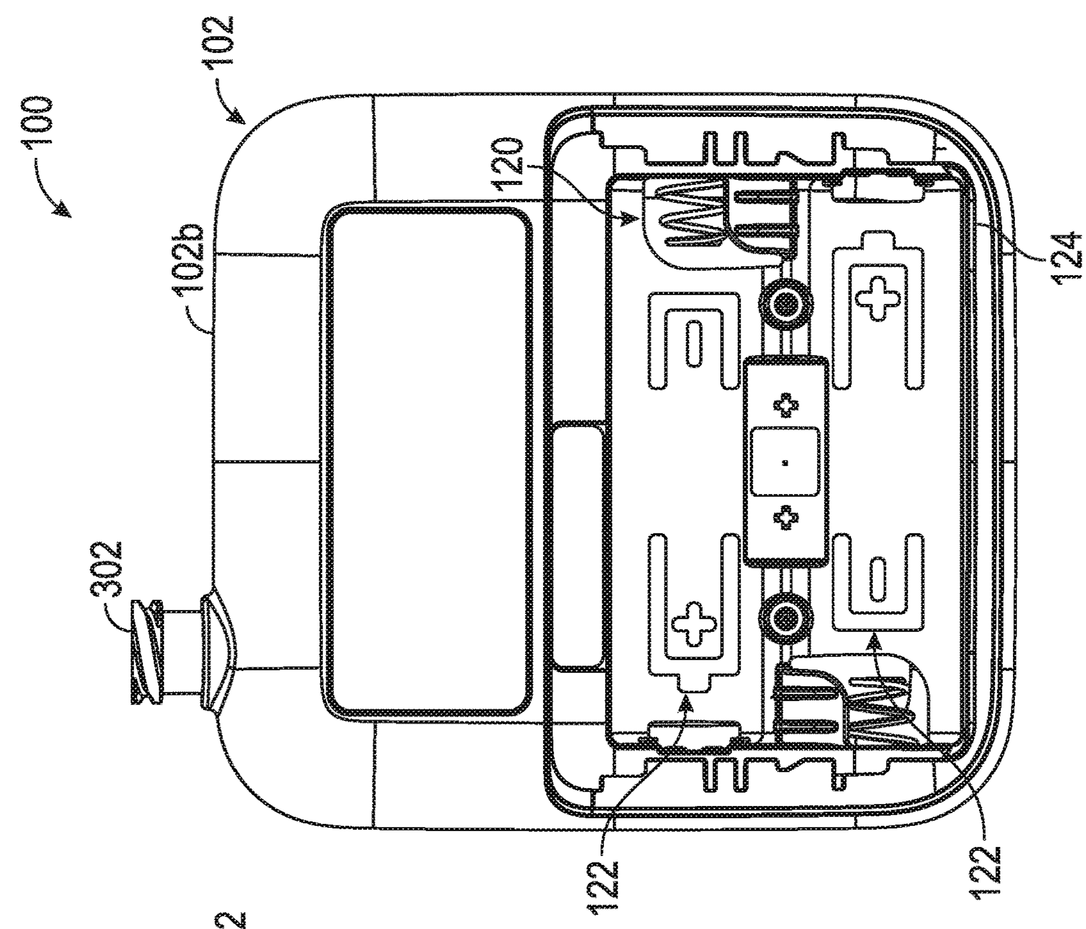
FIG. 10 is a rear view of the outer housing of FIG. 9, with a cover removed to expose cavity within the outer housing.
Figure 9:
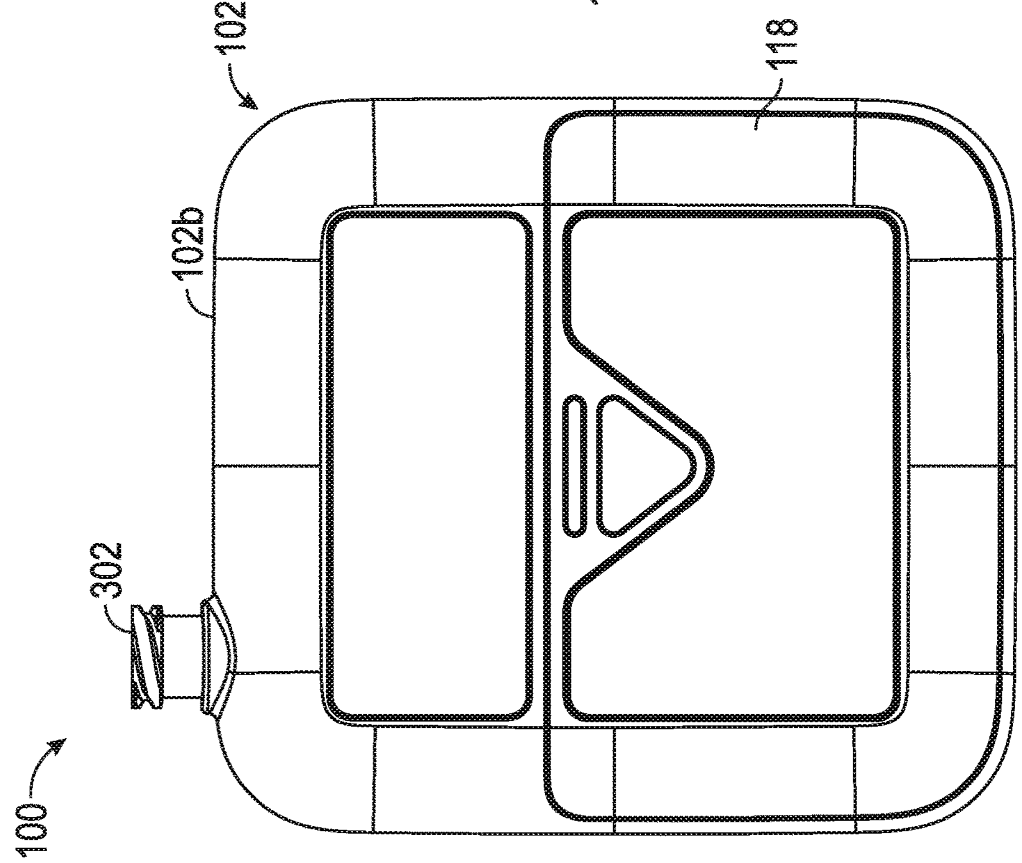
FIG. 9 is a rear view of the outer housing of FIG. 1, without the optional mounting component.

FIGS. 9 and 10 illustrate rear elevation views of the pump system 100 without the optional mounting component 104 attached to the outer housing 102 according to some embodiments. As shown in the illustrated embodiment, the rear portion 102*b* of the outer housing 102 can include a removable cover 118 for placement over a cavity 120. The cavity 120 can include one or more recesses 122 designed to receive one or more power sources, such as batteries, for powering the device. In some embodiments, an outer periphery 124 of the cavity 120 can include features which can cooperate with respective features of the cover 118 to reduce the likelihood that moisture will enter the cavity 120. For example, in some embodiments, the outer periphery 124 can include a rib along the bottom periphery, a side periphery, a top periphery, or a combination of one or more peripheries to reduce the likelihood of moisture ingress into the cavity 120. In some embodiments, the outer periphery 124 can include a recess along the bottom periphery, a side periphery, a top periphery, or a combination of one or more peripheries to redirect moisture, such as water droplets, away from the cavity 120.

Figure 12:
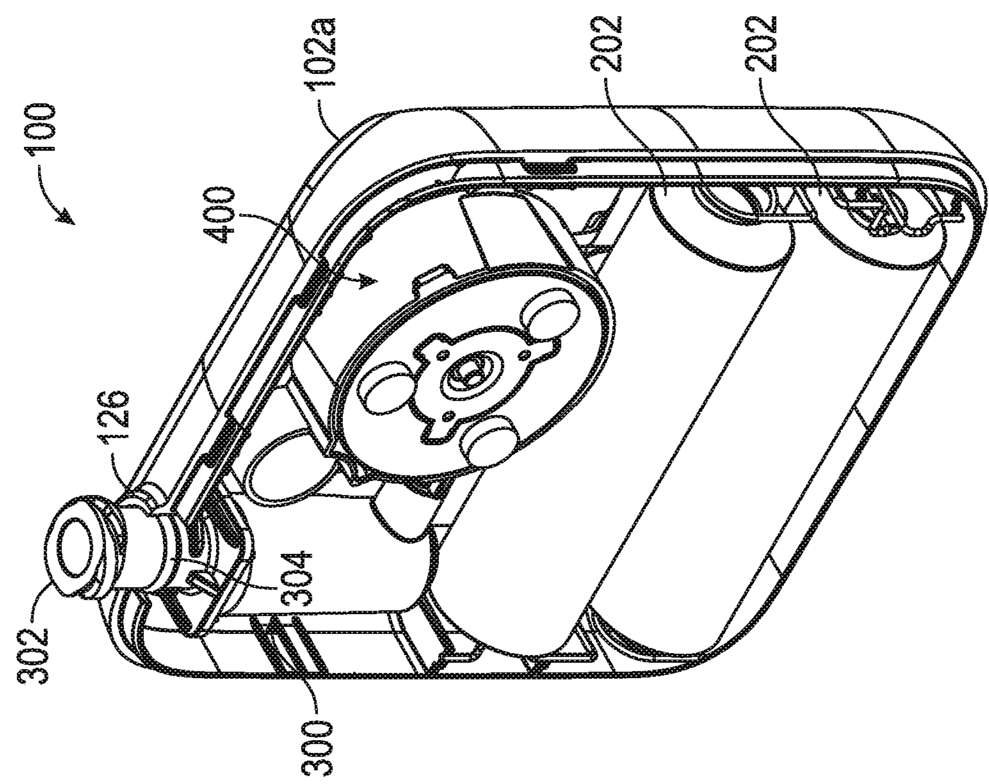
FIG. 12 is a rear perspective view of the outer housing of FIG. 1, with a rear portion of the outer housing removed to expose an embodiment of a circuit board and pump assembly.
Figure 11:
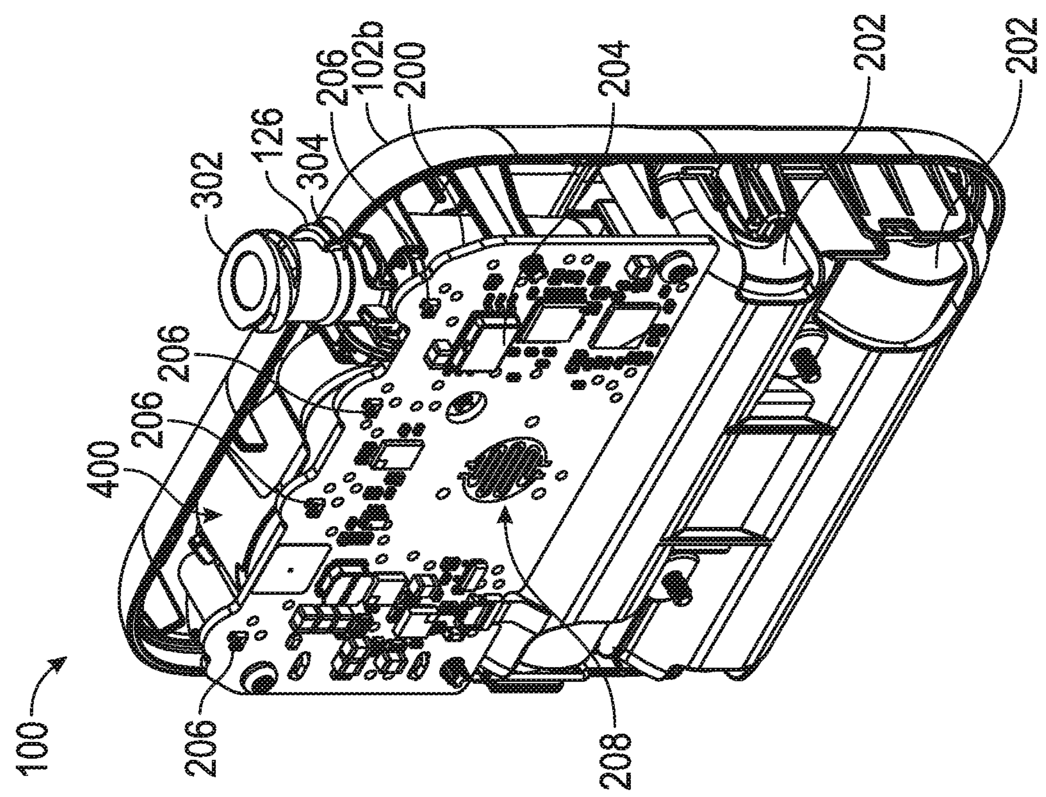
FIG. 11 is a front perspective view of the outer housing of FIG. 1, with a front portion of the outer housing removed to expose an embodiment of a circuit board and pump assembly.
Figure 13:
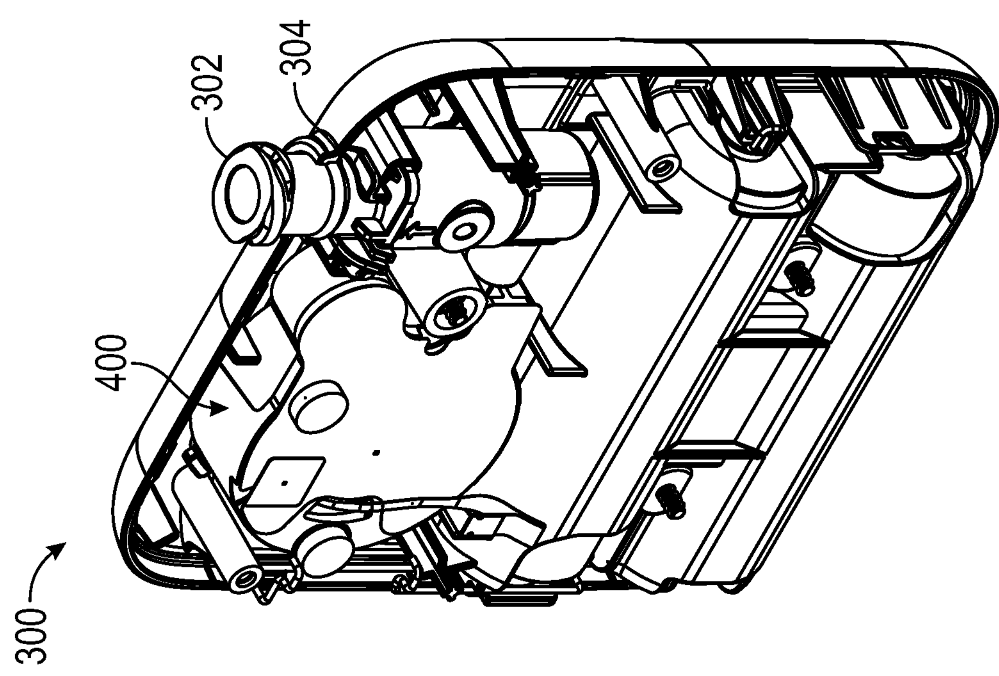
FIG. 13 is a front perspective view of the outer housing of FIG. 1, with a front portion of the outer housing and the circuit board removed to expose the pump assembly.

FIGS. 11 and 12 illustrate perspective views of a pump system 100 with portions of the outer housing 102 removed to expose an embodiment of a circuit board 200, an intake manifold 300, and a source of negative pressure such as a pump assembly 400 according to some embodiments. FIG. 13 illustrates a perspective view of an embodiment of pump system 100 with a front portion of the outer housing 102 removed as well as the circuit board 200 to expose the intake manifold 300 and pump assembly 400. As shown in the illustrated embodiment, the circuit board 200, the intake manifold 300, or the pump assembly 400 can be positioned within or supported by the outer housing 102.

The control board 200 can be designed to control the function of the pump system 100 such as the pump assembly 400. The control board 200 can be designed to mechanically support and electrically connect various electrical/electronic components of the pump system 100. For example, in some embodiments, the control board 200 can connect one or more batteries 202 to the pump assembly 400 to provide power to operate the pump assembly 400. In some embodiments, the control board 200 can include a pressure monitor 204. The pressure monitor 204 can be supported by the control board 200 and can be designed to monitor a level of pressure in a fluid flow passageway. The control board 200, in conjunction with the pressure monitor 204, can be designed to protect the pump assembly 400 from exceeding a predefined threshold pressure or can be designed to maintain a target pressure at the wound. In some implementations, the control board may be a printed circuit board assembly (PCBA), which can be a PCB having one or more electronic components electrically coupled to the PCB.

The circuit board 200 can be designed to cut power to the pump assembly 400 if the pressure reading reaches a predetermined value, and be designed to resume when the pressure level drops below the predetermined value or a second predetermined value that can be higher or lower than the first predetermined value. Additionally, the control board 200 can be programmed to prevent such over-pressurization.

The control board 200 can include indicator lights, audible alarms, or a combination of such features. For example, the control board 200 can include indicator lights in the form of one or more LEDs 206. As discussed above in connection with FIGS. 1-8, the one or more LEDs 206 can be used to illuminate one or more icons 114 of the display 112 on the outer housing 102. In some embodiments, each LED 206 can correspond to one or more icons 114. The control board 200 can have one or more features 208 (for example, pressure sensitive switch(es)) to receive an input from the control button 116.

FIG. 13 illustrates a front perspective view of a pump system 100 with a front portion of the outer housing 102 removed as well as the control board 200, to expose the intake manifold 300 and the pump assembly 400. As shown in the illustrated embodiment, the manifold 300 and the pump assembly 400 can be positioned within or supported by one or more portions of the outer housing 102.

In any of the embodiments disclosed herein, the control board 200 can be a flexible circuit board or can have one or more flexible components. A flexible circuit board is generally a patterned arrangement of printed circuitry and components that utilizes flexible based material with or without flexible overlay. These flexible electronic assemblies can be fabricated using the same components used for rigid printed circuit boards, but allowing the board to conform to a desired shape (flex) during its application. In their simplest form, flexible circuits are PCBs made of materials that allow for a non-planar positioning within the end product. Typical materials a polyimide-based, and can go under trade names such as Kapton (DuPont). Additionally, any of the control boards or controllers disclosed herein can have a combination of flexible and rigid substrates laminated into a single package.

Figure 15:
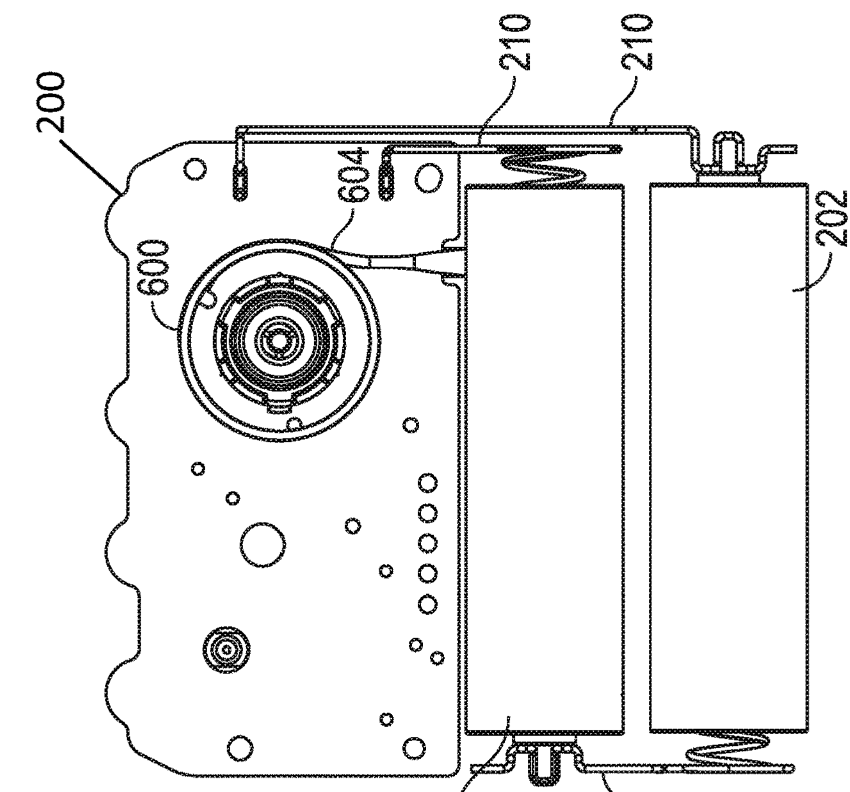
FIG. 15 is a rear view of the circuit board of FIG. 11.
Figure 14:
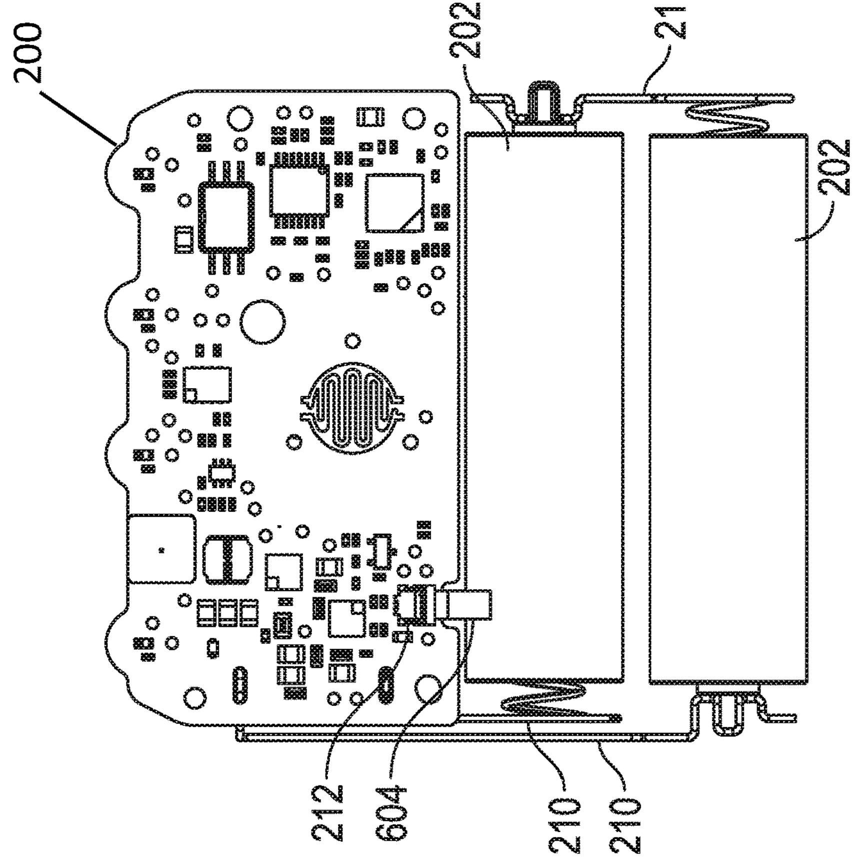
FIG. 14 is a front view of the circuit board of FIG. 11.

FIGS. 14 and 15 are various views illustrating wiring of the pump system 100 within the outer housing 102 according to some embodiments. As shown in the illustrated embodiment, the pump system 100 can include terminals 210 for connecting the circuit board 200 to a power source, such as batteries 202. The circuit board 200 can route power from the power source to a coil via an electrical conduit 604 attached to a connector 212 of the circuit board 200. In some embodiments, the electrical conduit 604 can be a flexible printed circuit (FPC) to facilitate assembly. In some embodiments, the electrical conduit 604 can be connected directly to the coil. For example, the ends of the FPC corresponding to a positive and negative terminal can be attached, such as via soldering or via adhesives, to ends or terminals of the coil. For example, the coil can have two terminals that can be soldered to two corresponding solder pads of the FPC. However, the wire used to manufacture the coil can be protected by an insulation layer and a self-bonding coating layer that can make manual soldering difficult or unreliable since manual soldering can expose the FPC to temperatures of 400 degrees Celsius for too long a time, which can damage the FPC substrate. To mitigate this problem, in some embodiments, a micro welding process can be used to electrically connect the FPC to the two terminals of the coil. In micro welding, a high current spike can be generated for a few milliseconds between the terminals of the coil and the pads of the FPC. The current spike can result in a localized temperature spike that can vaporize the insulating and self-bonding layers of the wire so that the wire of the coil can be bonded to the pads of the FPC. For example, the temperature spike can be 400 degrees Celsius or higher. However, because the temperature spike is limited to a few milliseconds using the micro welding process, the FPC substrate is not damaged.

Figure 17:
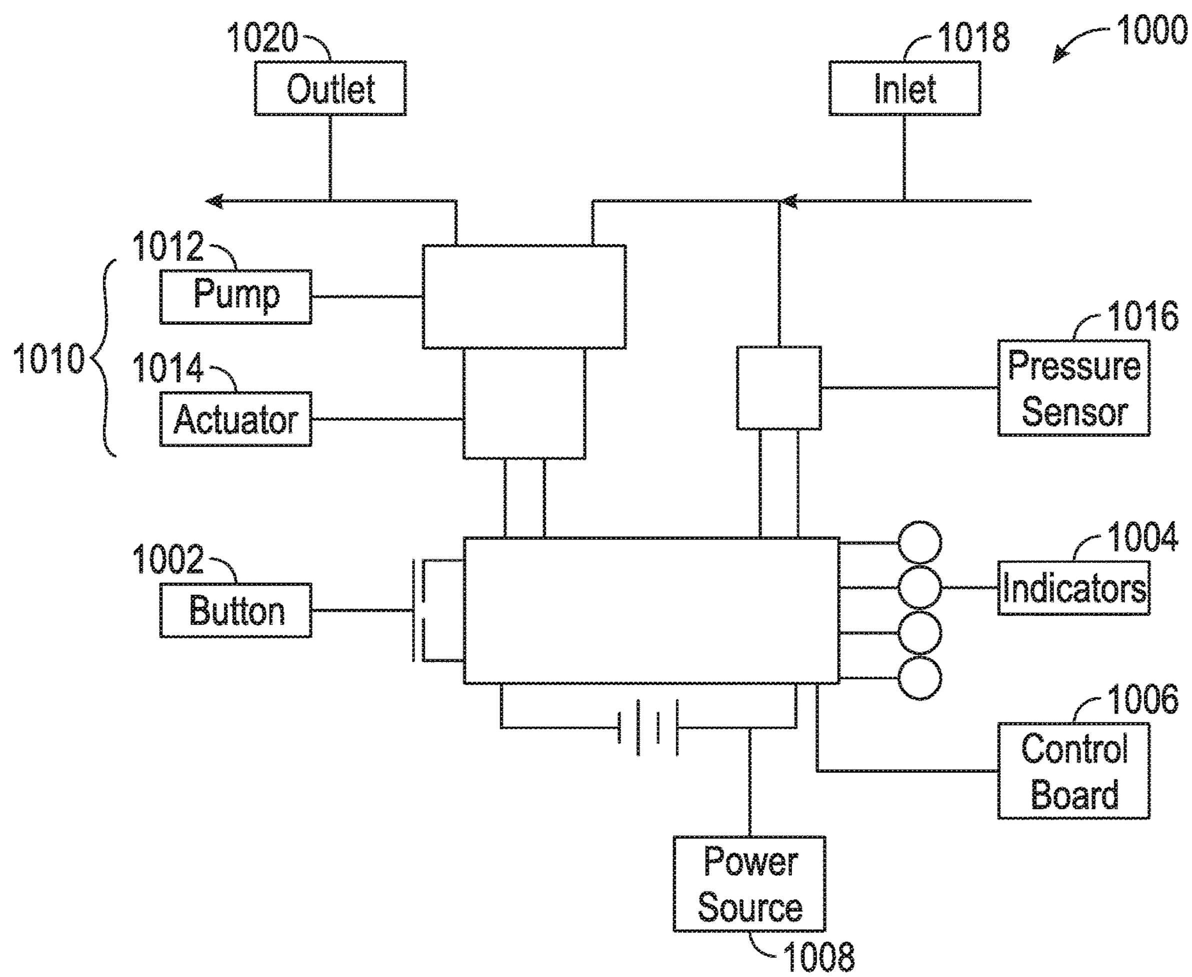
FIG. 17 is a schematic of a pump system according to some embodiments.

FIG. 17 illustrates a schematic of a pump system 1000 according to some embodiments. In some embodiments, the pump system 1000 can have any of the same or similar components, features, materials, sizes, configurations, and other details of any other pump system embodiments disclosed or incorporated by reference herein, including the embodiment of the pump system 100 described above. In some embodiments, the pump system 1000 can be miniaturized and portable, although larger conventional portable or non-portable (for example, wall suction) pumps can also be used.

As shown in the illustrated embodiment, the pump system 1000 can include a switch or a button 1002, one or more indicators 1004, and a control board 1006. The button 1002 or the one or more indicators 1004 can be in electrical communication with the control board 1006. As is explained in further detail below, in some embodiments the button 1002 can be used for any suitable purpose for controlling an operation of the pump system 1000. For example, button 1002 can be used to activate the pump system 1000, pause the pump system 1000, clear system indicators 1004, or be used for any other suitable purpose for controlling an operation of the pump system 1000. Button 1002 can by any type of switch or button, such as a touchpad, touch screen, keyboard, and so on. In some embodiments, the button 1002 can be a press button. For example, the button 1002 can be similar to button 116 of pump system 100.

In some embodiments, the one or more indicators 1004 can indicate one or more operating or failure conditions of the pump system 1000. In some embodiments, each of the one or more indicators 1004 can provide an indication regarding a different operating or failure condition. For example, an active (for example, lit) indicator 1004 can represent normal operation. Another indicator 1004, for example a dressing indicator, can provide an indication as to presence of leaks in the system. For example, an active (for example, lit) dressing indicator can represent a leak. Another indicator 1004, for example a dressing capacity indicator, can provide an indication as to the remaining fluid capacity of a wound dressing. For example, an active (for example, lit) dressing capacity indicator can represent that the wound dressing is at or nearing capacity. Another indicator 1004, such as a battery indicator, can provide an indication as to remaining capacity or life of a power source, such as batteries. For example, an active (for example, lit) battery indicator can represent a low capacity. In some embodiments, an indicator 1004 can represent a combination of the above operating or failure conditions of the pump system 1000 or other operating or failure conditions.

With continued reference to the embodiment of pump system 1000 illustrated in FIG. 17, in some embodiments, the one or more indicators 1004 can be icons. For example, the one or more indicators 1004 can be similar to the icons 114 of pump system 1004 and can be activated (for example, lit) via an illumination source such as LEDs 206 of pump system 100. In some embodiments, the one or more indicators 1004 can be of a different color, two different colors (for example, two indicators can share the same color), or the same color. Although the pump system 1000 can include four icons and a push play/pause button, other configurations, locations, and types of indicators, alarms, and switches can alternatively be used. In some embodiments, the pump system 1000 can include visual, audible, tactile, and other types of indicators or alarms configured to signal to the user various operating conditions. Such conditions include system on/off, standby, pause, normal operation, dressing problem, leak, error, and the like. The indicators can include speakers, displays, light sources, etc., or combinations thereof.

As shown in the illustrated embodiment, the pump system 1000 can be powered by a power source 1008 such as a battery power cell. The pump system 1000 can also include a source of negative pressure 1010, such as a pump assembly having a pump 1012 powered by an electric motor 1014, and a pressure sensor 1016, such as pressure monitor 204 of pump system 100. In some embodiments, the pump system 1000 can include an inlet 1018 to connect the pump system 1000 to a wound dressing. For example, in some embodiments, the inlet 1018 can be a connector for connecting the inlet 1018 to a conduit which is in fluid communication with a wound dressing. The connector can be similar to connector 302 of pump system 100. The pump 1012 can be connected to an outlet 1020. In some embodiments, the outlet 1020 can vent air to the atmosphere. In some embodiments, a filter (not shown) can be interposed between the outlet and the atmosphere. The filter can provide filtration of the air prior to venting to the atmosphere. In some embodiments, the filter can be a bacterial filter, odor filter, etc. or any combination thereof. In some embodiments, a dampening component (not shown), such as a noise dampening component, can be interposed between the outlet and the atmosphere. The dampening component can reduce the noise generated by the pump system 1000 during operation. In some embodiments, the dampening component can be similar to dampening component 902 of pump system 100.

In some embodiments, the pump system 1000 can include a valve (not shown), such as a one-way valve, in a flow passage between the wound dressing and an inlet of the pump 1012. The valve can help maintain a level of negative pressure when the pump 1012 is not active. In some embodiments, the valve can help avoid leaks. The valve can also help prevent fluids or exudate aspirated or removed from the wound from entering the pump system 1000.

Figure 18:
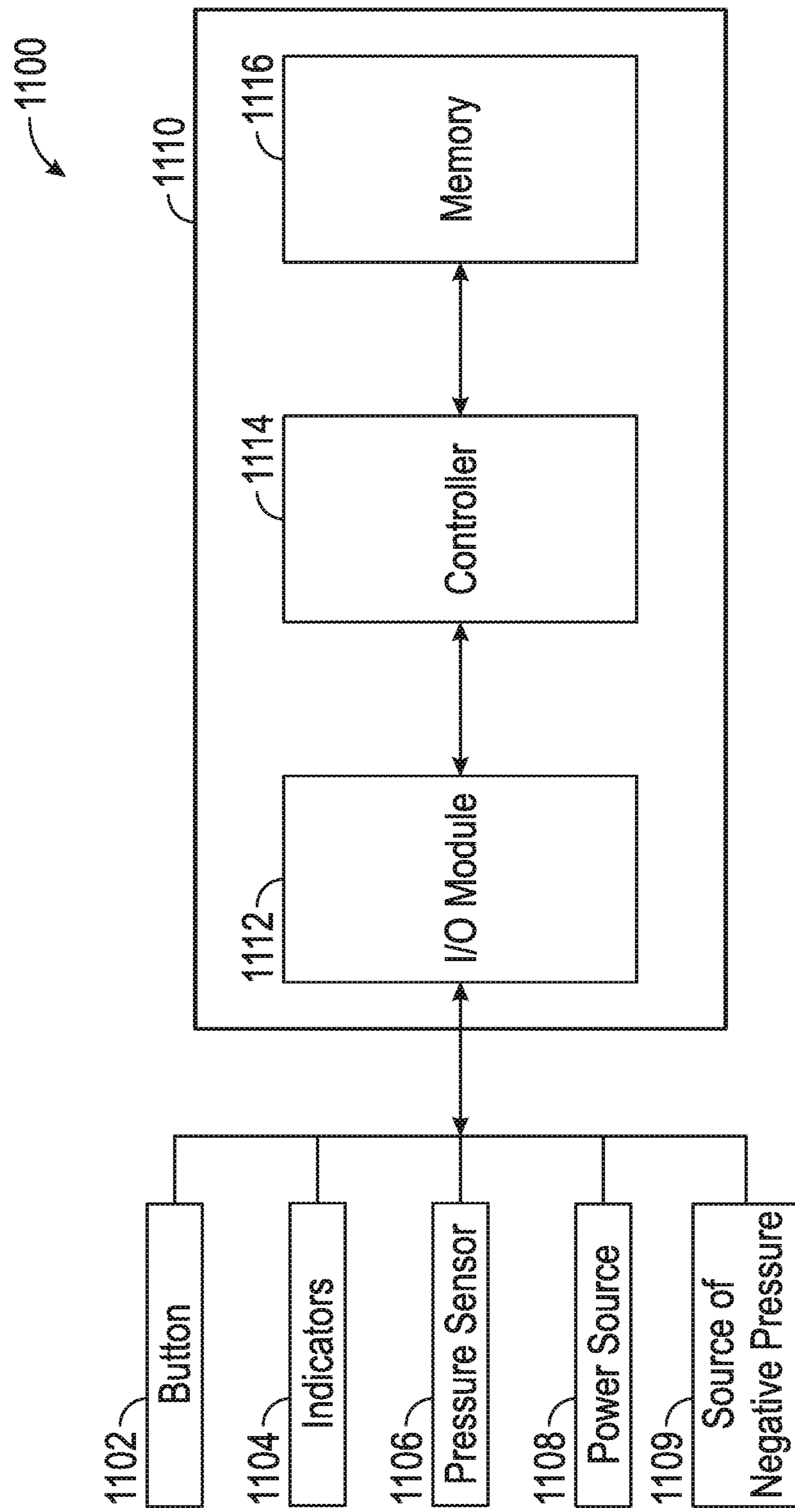
FIG. 18 is a schematic of a pump system according to some embodiments.

FIG. 18 illustrates an electrical component schematic of a pump system 1100 according to some embodiments. In some embodiments, the pump system 1100 can have any of the same or similar components, features, materials, sizes, configurations, and other details of any other pump system embodiments disclosed or incorporated by reference herein, including the embodiment of the pump system 100, 1000 described above.

Pump system 1100 can include one or more buttons 1102, one or more indicators 1104, one or more pressure sensors 1106, power source 1108, a source of negative pressure 1109, or a module 1110. In some embodiments, the one or more buttons 1102, one or more indicators 1104, one or more pressure sensors 1106, power source 1108, or source of negative pressure 1109 can be similar to button 1002, indicators 1004, pressure sensor 1016, power source 1008, or source of negative pressure 1010 of pump system 1000.

Module 1110, which can be a control board (for example, PCBA), can include an input/output (I/O) module 1112, controller 1114, and memory 1116. In some embodiments, module 1110 can include additional electric/electronic components, for example, fuse or fuses, or external memory (such as flash-memory). The controller 1114 can be a microcontroller, processor, microprocessor, etc. or any combination thereof. For example, the controller 1114 can be of the STM8L MCU family type from ST Microelectronics, such as STM8L 151G4U6 or STM8L 151K6U6TR, or of MC9S08QE4/8 series type from Freescale, such as MC9S08QE4CWJ. Preferably, the controller 1114 is a low power or ultra low power device, but other types of devices can alternatively be used. Memory 1116 can include one or more of volatile or nonvolatile memory modules, such as one or more of read-only memory (ROM), write once read many memory (WORM), random access memory (for example, SRAM, DRAM, SDRAM, DDR, etc.), solid-state memory, flash memory, Magnetoresistive random-access memory (MRAM), magnetic storage, etc. or any combination thereof. Memory 1116 can be configured to store program code or instructions (executed by the controller), system parameters, operational data, user data, etc. or any combination thereof. In some embodiments, one or more components of the pump system 1100 can form part of a monolithic unit. In some embodiments, the memory 1116 can be 16 megabits, 32 megabits, or of another suitable size depending on the amount of data configured to be logged during operation of the pump system 1100. In some embodiments, the logged data can be stored to advantageously gather information that is relevant to clinical trial(s). In some embodiments, one or more components of the pump system 1100 can be removable from other components. For example, in some embodiments, memory 1116 can be removable flash memory.

Figure 19:
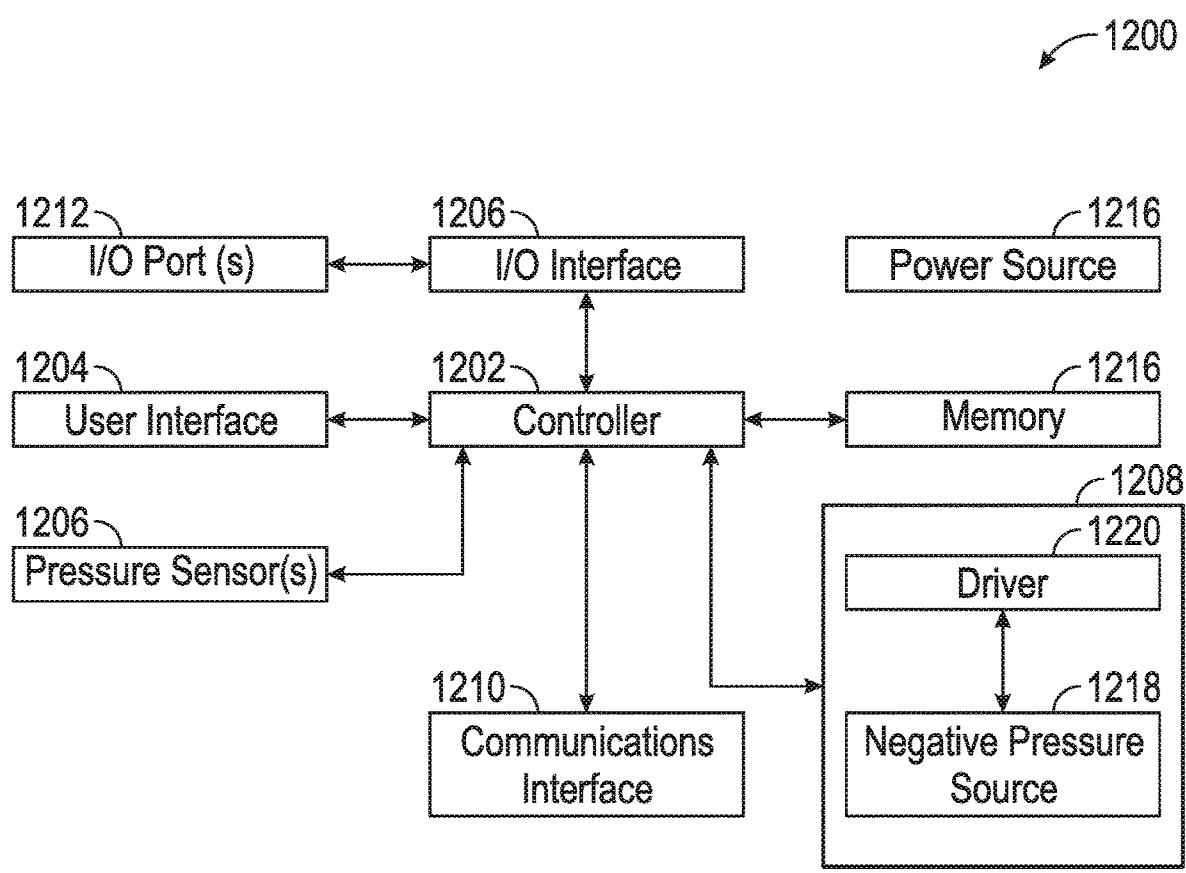
FIG. 19 is a schematic of a pump system according to some embodiments.

FIG. 19 illustrates an electrical component schematic of a pump system 1200 according to some embodiments. In some embodiments, the pump system 1200 can have any of the same or similar components, features, materials, sizes, configurations, and other details of any other pump system embodiments disclosed or incorporated by reference herein, including the embodiments of the pump systems 100, 1000, 1100. Electrical components can operate to accept user input, provide output to the user, operate the pump system and the source of negative pressure, provide network connectivity, and so on. Electrical components can be mounted on one or more PCBs (not shown). The pump system can include a controller or processor 1202. In any embodiments disclosed herein, the controller 1202 can be a general purpose processor, such as a low-power processor. In other embodiments, the controller 1202 can be an application specific processor. In any embodiments disclosed herein, the controller 1202 can be configured as a "central" processor in the electronic architecture of the pump system, and the controller 1202 can coordinate the activity of other controllers, such as a user interface controller 1204, I/O interface controller 1206, negative pressure control module 1208, communications interface controller 1210, and the like.

The pump system 1200 can also include a user interface controller or processor 1204 which can operate one or more components for accepting user input and providing output to the user, such as buttons, indicators (for example, LEDs), displays, etc. Input to the pump system 1200 and output from the pump system 1200 can be controlled via one or more input/output (I/O) ports 1212 controlled by a I/O interface module or controller 1206. For example, the I/O module 1206 can receive data from one or more I/O ports 1212, such as serial, parallel, hybrid ports, expansion ports, and the like. In any embodiments disclosed herein, I/O ports 1212 include one or more of USB ports, SD ports, Compact Disc (CD) drives, DVD drives, FireWire ports, Thunderbolt ports, PCI Express ports, and the like. The controller 1202, along with other controller or processors, can store data in one or more memory modules 1214, which can be internal or external to the system 1200. Any suitable type of memory can be used, including volatile or non-volatile memory, such as RAM, ROM, WORM, magnetic memory, solid-state memory, MRAM, and the like or any combination thereof. The pump system 1200 can be powered by a power source 1216, which can comprise one or more disposable or rechargeable batteries, power from mains, etc. The power source 1216 can be internal or external to the system 1200.

With continued reference to the embodiment of pump system 1200 illustrated in FIG. 19, in some embodiments, a negative pressure or pump control module 1208 can be configured to control the operation of a negative pressure source 1218. The negative pressure source 1218 can be a voice coil pump. Other suitable pumps include diaphragm pumps, peristaltic pumps, rotary pumps, rotary vane pumps, scroll pumps, screw pumps, liquid ring pumps, pumps operated by a piezoelectric transducer, and the like. The pump control module 1208 can include a driver module 1220 configured to control the operation of the negative pressure source 1218. For example, the driver module 1220 can provide power to the negative pressure source 1218. Power can be provided in a form of a voltage or current signal. In any embodiments disclosed herein, the driver module 1220 can control the negative pressure source 1218 using pulse-width modulation (PWM). A control signal for driving the negative pressure source 1218 (or pump drive signal) can be a 0-100% duty cycle PWM signal. The drive module 1220 can control the negative pressure source 1218 using any other suitable control, such as proportional-integral-derivative (PID).

The controller 1202 can receive information from one or more sensors, such as pressure sensors 1206, placed in a suitable location in a fluid flow path, such as pressure monitor 204 placed within intake manifold 300 of pump system 100. In any embodiments disclosed herein, the controller 1202 can measure pressure in the fluid flow path, using data received from one or more pressure sensors 1206, calculate the rate of fluid flow, and control the negative pressure source 1218 so that desired level of negative pressure is achieved in a wound cavity or under the wound dressing. The desired level of negative pressure can be pressure set or selected by a user. Pressure measured by the one or more sensors can be provided to the controller 1202 so that the controller can determine and adjust the pump drive signal to achieve the desired negative pressure level. In any embodiments disclosed herein, the tasks associated with controlling the negative pressure source 1218 can be offloaded to the pump control module 1208, which can include one or more controllers or processors.

In any embodiments disclosed herein, it may be advantageous to utilize multiple processors for performing various tasks. In any embodiments disclosed herein, a first processor can be responsible for user activity and a second processor can be responsible for controlling the negative pressure source. This way, the activity of controlling the negative pressure source, which may necessitate a higher level of responsiveness, can be offloaded to a dedicated processor and, thereby, will not be interrupted by user interface tasks, which may take longer to complete because of interactions with the user.

A communications interface controller or processor 1210 can be configured to provide wired or wireless connectivity. The communications processor 1210 can utilize one or more antennas (not shown) for sending and receiving data. In any embodiments disclosed herein, the communications processor 1210 can provide one or more of the following types of connections: Global Positioning System (GPS) technology, cellular or other connectivity, such as 2G, 3G, LTE, 4G, WiFi, Internet connectivity, Bluetooth, zigbee, RFID, and the like. Additionally, any embodiments disclosed herein can be configured to synchronize, upload, or download data to or from the pump apparatus to or from a portable data device, such as a tablet, smart phone, or other similar devices.

Connectivity can be used for various activities, such as pump system location tracking, asset tracking, compliance monitoring, remote selection, uploading of logs, alarms, and other operational data, and adjustment of therapy settings, upgrading of software or firmware, and the like. In any embodiments disclosed herein, the communications processor 1210 can provide dual GPS/cellular functionality. Cellular functionality can, for example, be 3G or 4G functionality. In such cases, if the GPS module is not be able to establish satellite connection due to various factors including atmospheric conditions, building or terrain interference, satellite geometry, and so on, the device location can be determined using the 3G or 4G network connection, such as by using cell identification, triangulation, forward link timing, and the like. In any embodiments disclosed herein, the pump system 1200 can include a SIM card, and SIM-based positional information can be obtained.

Protection of Negative Wound Pressure Therapy System Electronics

The electronics of a pump system, such as the pump systems 100, 1000, 1100, or 1200, can be constructed and positioned to improve the tolerance of the pump system to environmental conditions. The pump system desirably can operate electrically or mechanically properly or safely in various non-controlled environments like home healthcare, airborne, automobile, boats, train, metal detectors, active implantable device, and the like.

The pump system can be configured to withstand high levels of ESD and in multiples steps, such as contact: ±2 kV, ±4 kV, ±6 kV, ±8 kV or higher, and air: ±2 kV, ±4 kV, ±6 kV, ±8 kV±15 kV, ±30 kV or higher. The pump system can additionally or alternatively be configured to have high levels of magnetic immunity like with respect to 100 A/m, 150 A/m, 200 A/m, 400 A/m or higher, as well as high levels of RF immunity like with respect to 10 V/m, 20 V/m and higher. Additionally or alternatively, the pump system can withstand high levels of mechanical strain (for example, shock, vibration, drop, or the like) and high altitude environments (for example, airborne mechanical).

The pump system can, in some implementations, be defibrillation-proof (for instance, defibrillation-proof as an entire applied part), such as is defined under the IEC 60601-1 standard, another standard, or other industry-accepted criteria. The pump system can, for example, continue normal operation when monophasic or biphasic defibrillation shock is applied. The pump system may not change its performance or present false alarms under such conditions. Such a defibrillation-proof construction can be desirable because the pump system can then survive an external defibrillation shock in case a patient using the pump system goes into cardiac arrest. Moreover, the pump system can be defibrillator-proof while retaining usability (for example, not having a metal case, which may, for instance, add too much weight to the device).

One or more of the features described herein can enable the pump system to withstand high levels of ESD, have magnetic immunity or RF immunity, withstand high levels of mechanical strain, withstand high altitude environment, or be defibrillation-proof.

The pump system can include one or more PCBAs, which may each include a PCB that mechanically supports and electrically connects electronic components. Components, such as capacitors, resistors, or active devices, can be soldered on PCBs or embedded in substrate. PCBAs can be single-sided (one copper layer), double-sided (two copper layers) or multi-layer (outer and inner layers). Conductors on different layers are connected with vias. Multi-layer PCBAs allow for much higher component density. In one implementation, the pump system can include a PCBA having one or two layers. In yet another implementation, the pump system can include a PCBA having three or more layers, such as six layers.

The pump system can be constructed to electrically isolate certain internal device components and provide electromagnetic interference shielding (EMI) shielding and other forms of electrical isolation.

Figure 20A:
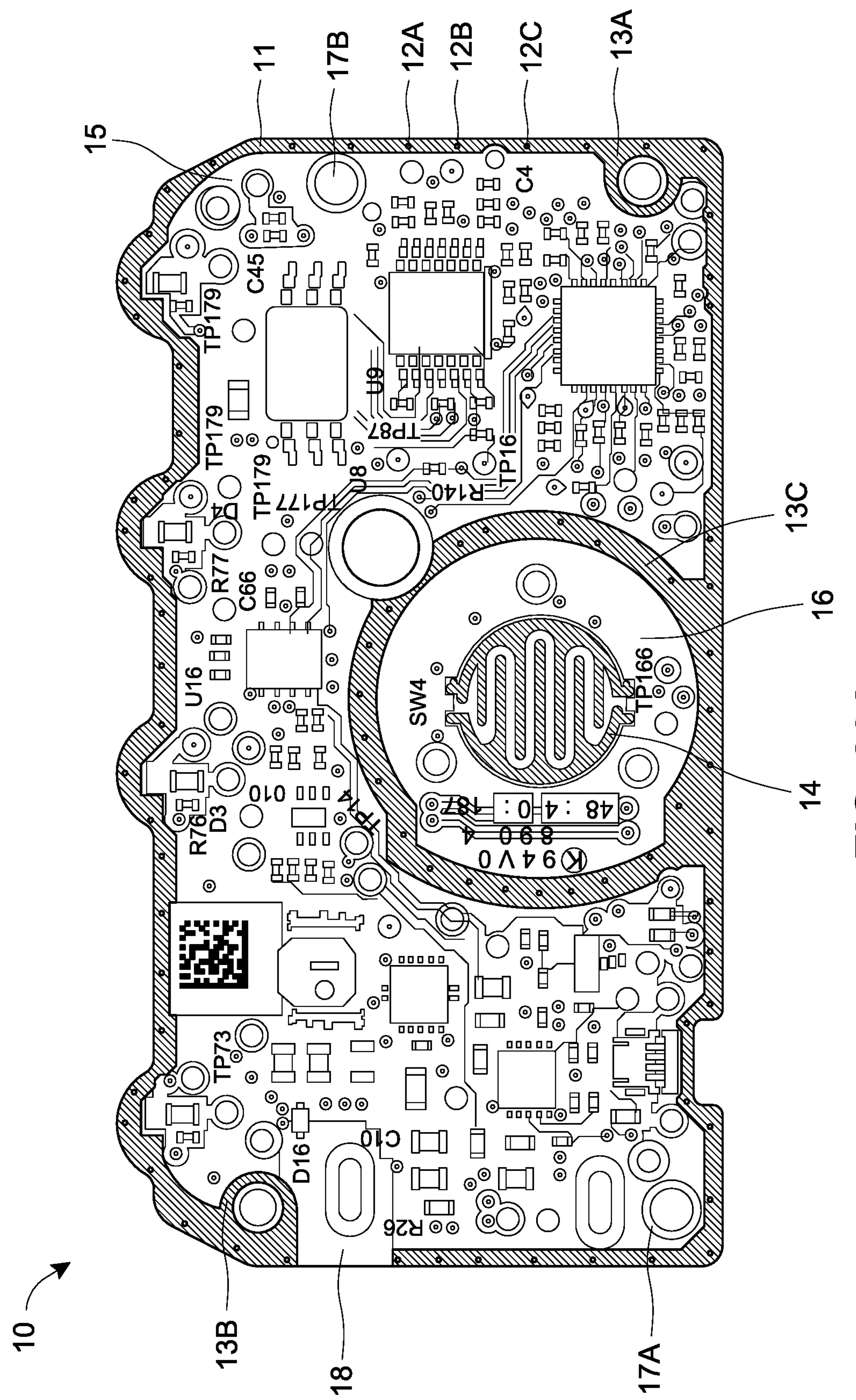
FIGS. 20A and 20B illustrate a front and back of a circuit board usable with pump systems like the pump systems of FIGS. 1, 17, 18, and 19.

FIG. 20A illustrates an example front of a PCBA 10 usable as part of a pump system, like one of the pump systems 100, 1000, 1100, or 1200. The PCBA 10 can, for instance, be an implementation of the circuit board 200. The PCBA 10 can differ from the circuit board 200 at least in that the PCBA 10 can include a conductive pathway 11, vias 12A, 12B, and 12C, portions 13A, 13B, and 13C, a conductive pathway 21, and vias 22A, 22B, and 22C.

The conductive pathway 11 can extend around all or part (for instance, 20%, 25%, 30%, 35%, 40%, 45%, 50%, 55%, 60%, 65%, 70%, 75%, 80%, 85%, 90%, or 95% of a length) of a perimeter or an edge of at least one side of the PCBA 10, is connected to ground of the pump system (for instance, to a negative voltage of a power supply), and serves to protect the PCBA 10 when the PCBA 10 is exposed to ESD by providing a discharge path. The conductive pathway 11 can include multiple vias, including the vias 12A, 12B, and 12C. The vias of the conductive pathway 11 can be pathways through the PCBA 10 that electrically link the conductive pathway 11 to a surface on an opposite side of the PCBA 10 through the layers of the PCBA 10. The vias of the conductive pathway 11 can be manufactured by drilling through the PCBA 10 and coating the inside of the drilled hole with a column of conductive material. The vias of the conductive pathway 11 can be spaced apart from one another between around 1 mm to 10 mm, such as around 2.5 mm, but can be spaced apart a lesser or greater spacing in some implementations.

The conductive pathway 11 can include the portions 13A and 13B that follow a path around holes in the PCBA 10 usable for inserting fasteners to secure the PCBA 10 to another component, such as a housing of the pump assembly. The conductive pathway 11 can include the portion 13C that follows a contact path 14 around an interface element, such as a button (for example, which can be an elastomer) responsive to user inputs, on the PCBA 10. The fasteners or the interface element can be nominally insulating, but at high voltages can become conductive. If an electrical discharge is applied through the fasteners or the interface element, then the electrical discharge can be desirably grounded to the portions 13A, 13B, and 13C.

The conductive pathway 11 can be separated from one or more components mounted to the PCBA 10 or conductive elements by insulating portions 15 and 16. The conductive pathway 11 may not extend around some holes in the PCBA 10, such as holes 17A and 17B that may be used for guiding the PCBA 10 into place rather than securing the PCBA 10 or usable for inserting fasteners that have relatively high breakdown voltages. As illustrated in FIG. 20A, the conductive pathway 11 can extend around the perimeter of the front of the PCBA 10 other than at an area 18 of the insulating portion 15, which may be near where a positive voltage of a power supply provides power to the PCBA 10. In some implementations, every layer of the PCBA 10 may be electrically grounded.

Figure 20B:
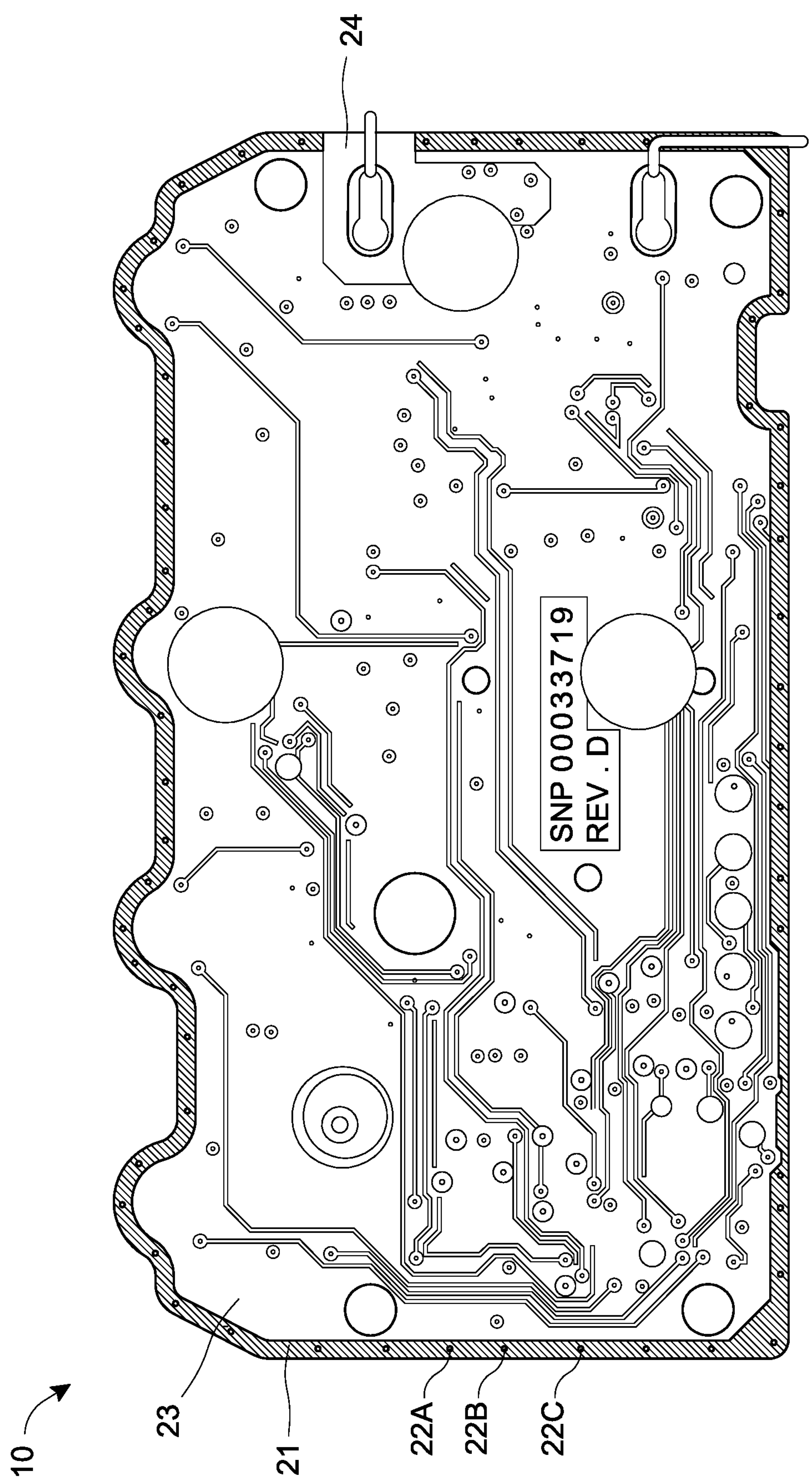

FIG. 20B illustrates an example back of the PCBA 10 with the conductive pathway 21 that includes multiple vias, such as the vias 22A, 22B, and 22C. The structure of the conductive pathway 21 and its vias can be similar to the structure of the conductive pathway 11 and its vias. The conductive pathway 21 can, moreover, be electrically connected to the conductive pathway 11 through the vias of the conductive pathways 11 and 21. The conductive pathway 21 can be separated from one or more components mounted to the PCBA 10 or conductive elements by an insulating portion 23. As illustrated in FIG. 20B, the conductive pathway 21 can extend around the perimeter of the back of the PCBA 10 other than at an area 24 of the insulating portion 23, which may be near where a positive voltage of a power supply provides power to the PCBA 10. In some implementations, the PCBA 10 may have a conductive pathway on one side of the PCBA 10 but not on the opposite side.

Figure 21A:
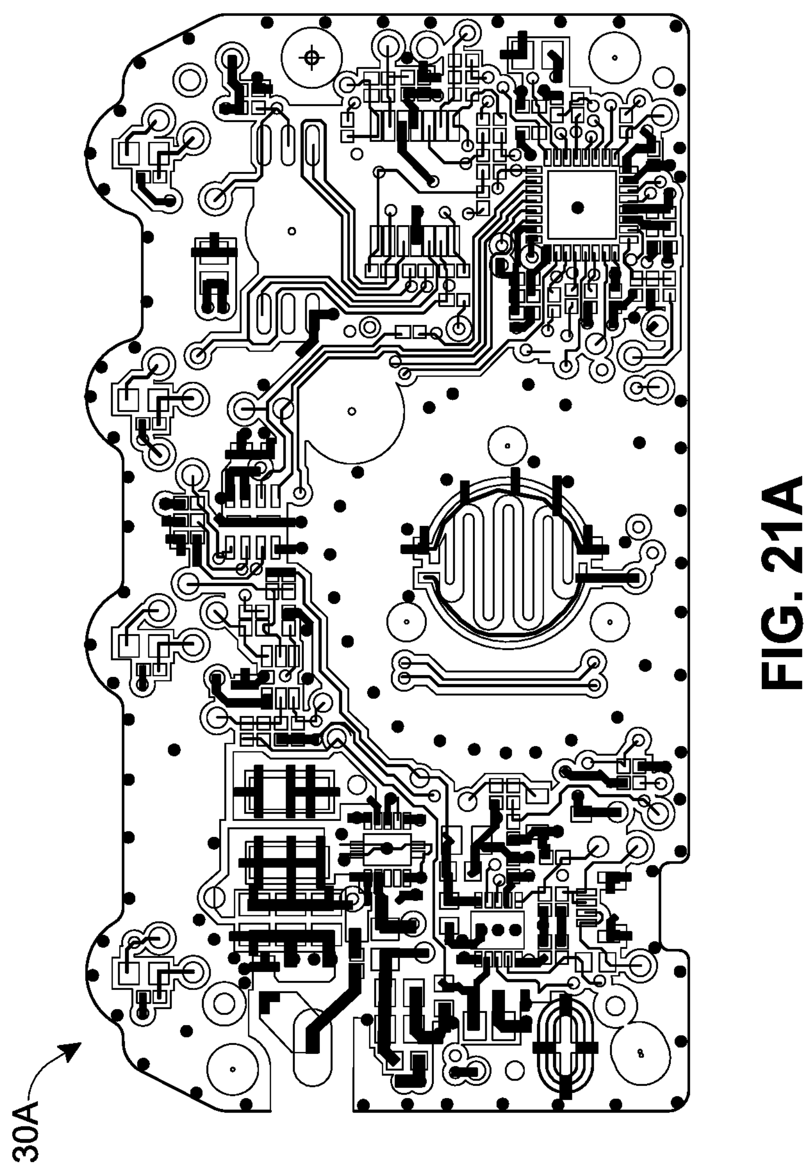
FIGS. 21A, 21B, 21C, and 21D illustrate art films of different layers of a circuit board, such as the circuit board of FIGS. 20A and 20B.
Figure 21B:
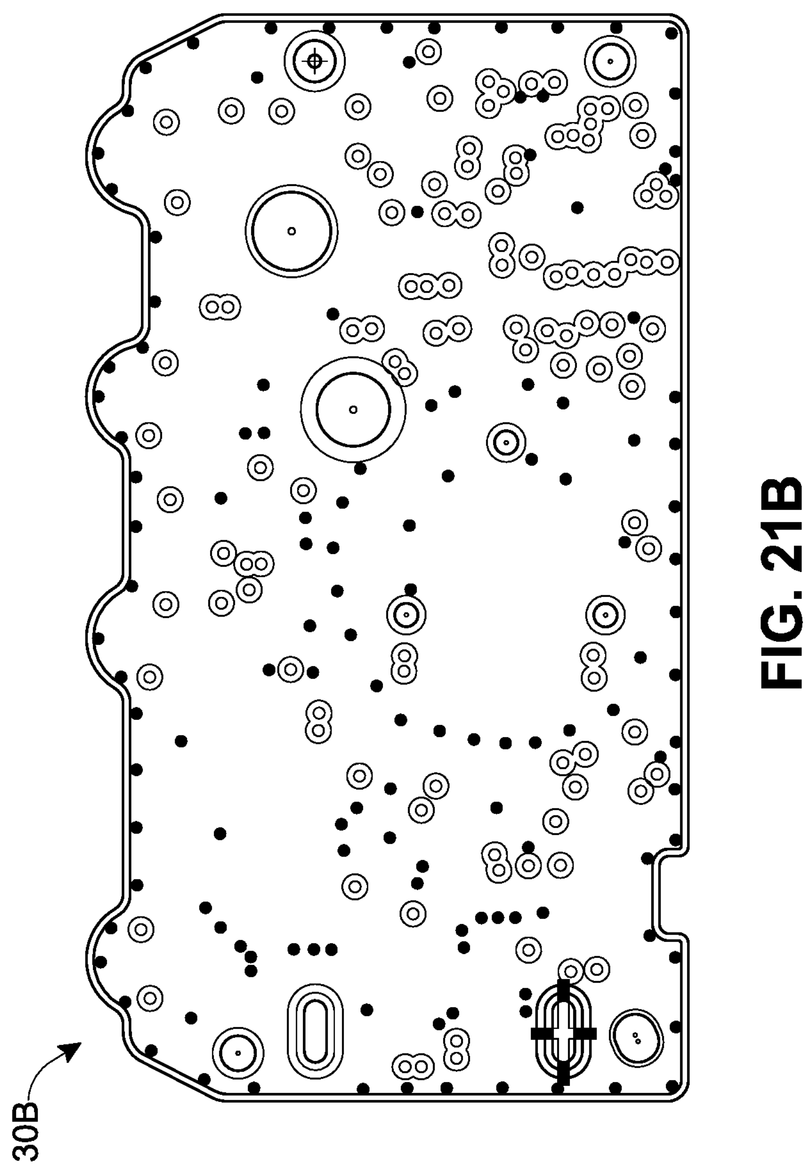
Figure 21C:
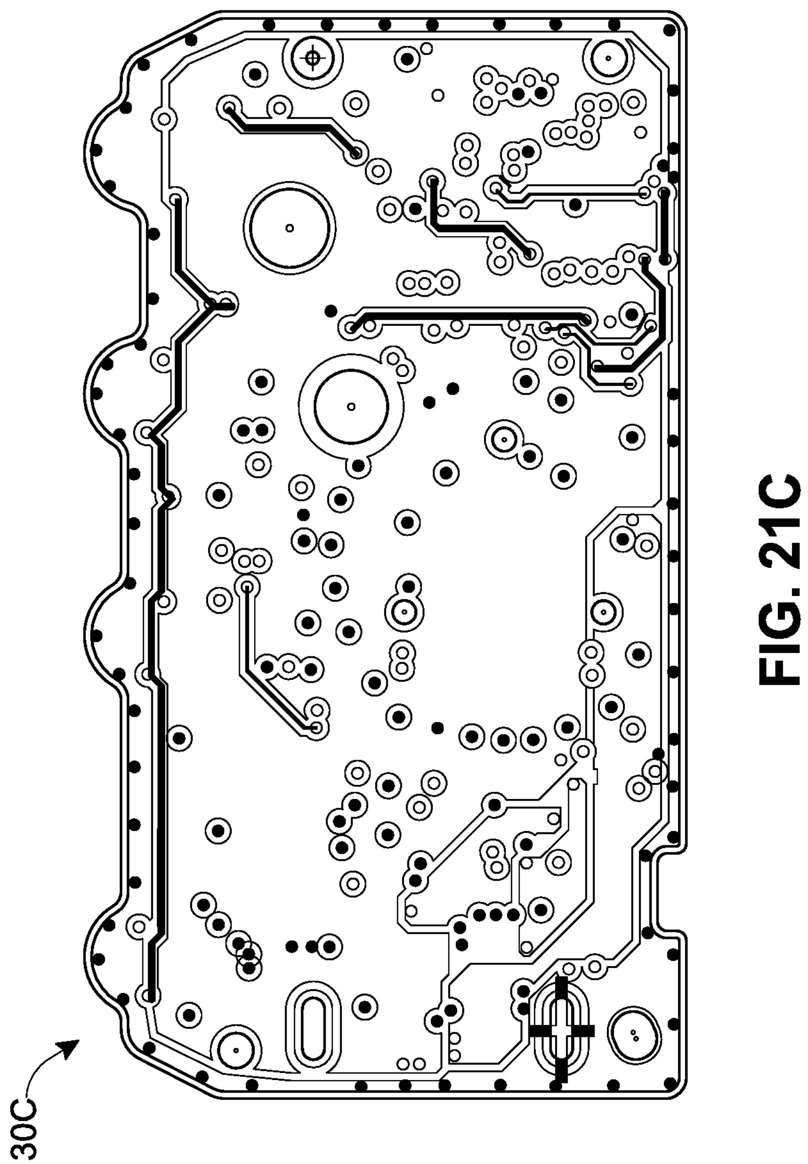
Figure 21D:
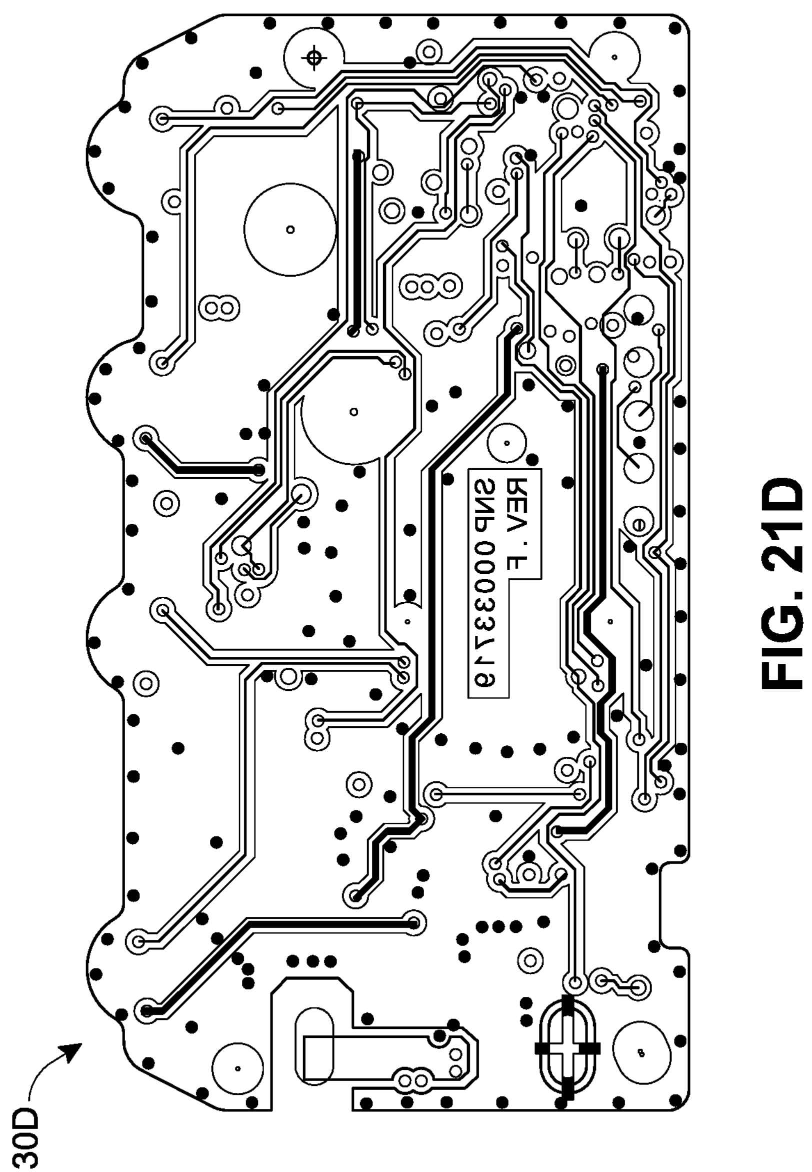

FIG. 21A illustrates example art film of a first layer 30A of the PCBA 10. The first layer 30A can be a top layer of the PCBA 10. FIG. 21B illustrates example art film of a second layer 30B of the PCBA 10. FIG. 21C illustrates example art film of a third layer 30C of the PCBA 10. FIG. 21D illustrates example art film of a fourth layer 30D of the PCBA 10. The fourth layer 30D can be a bottom layer of the PCBA 10.

Figure 22A:
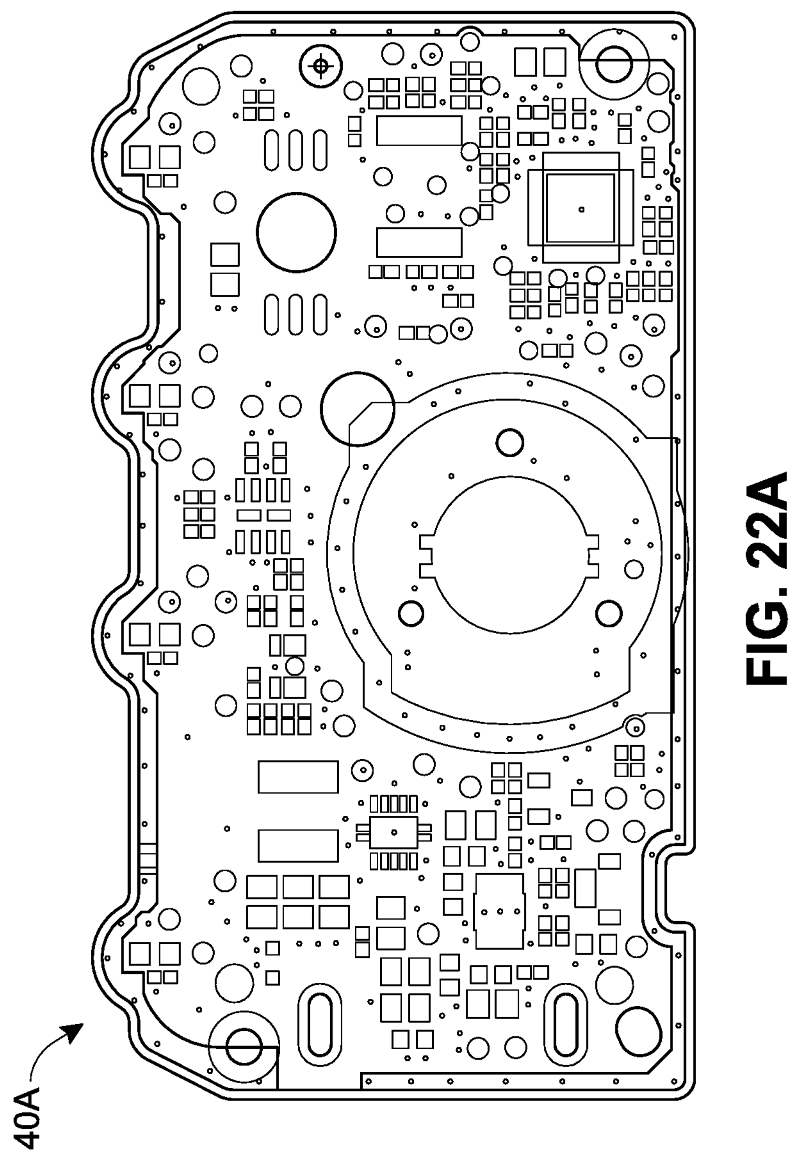
FIGS. 22A and 22B illustrate solder masks for a top side and bottom side of a circuit board, such as the circuit board of FIGS. 20A and 20B.
Figure 22B:
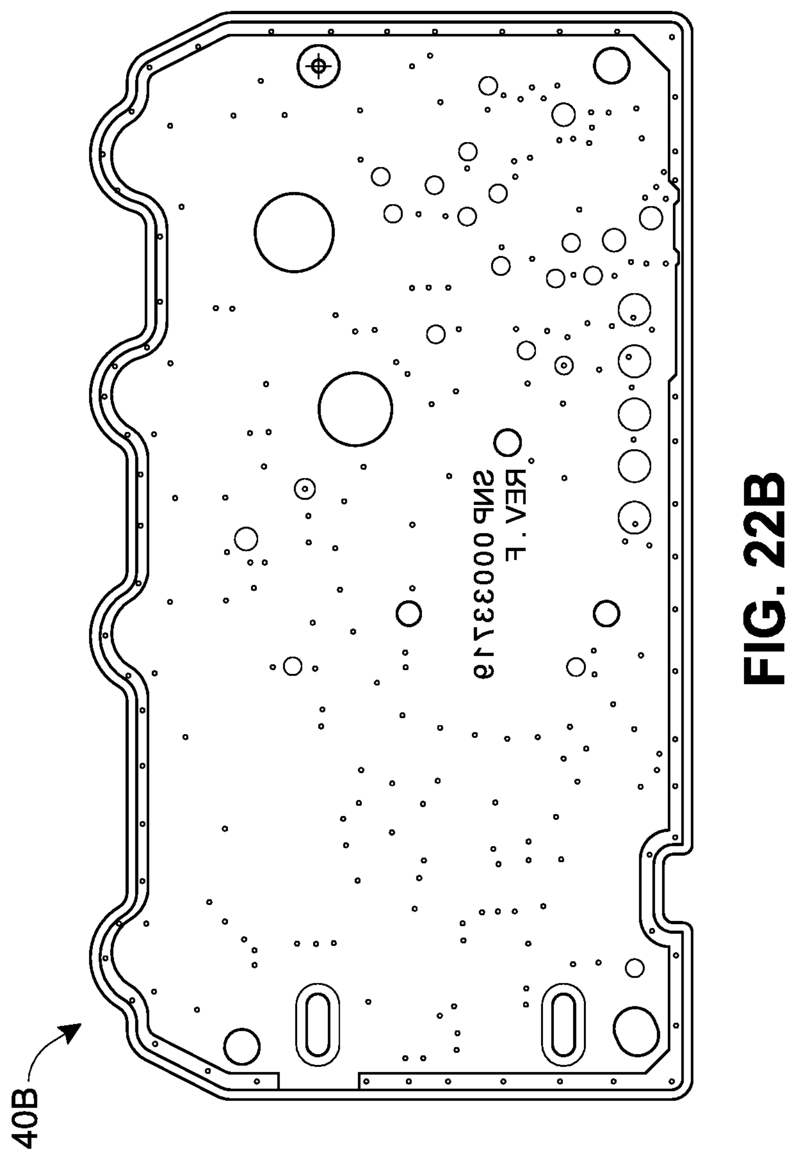
Figure 23:
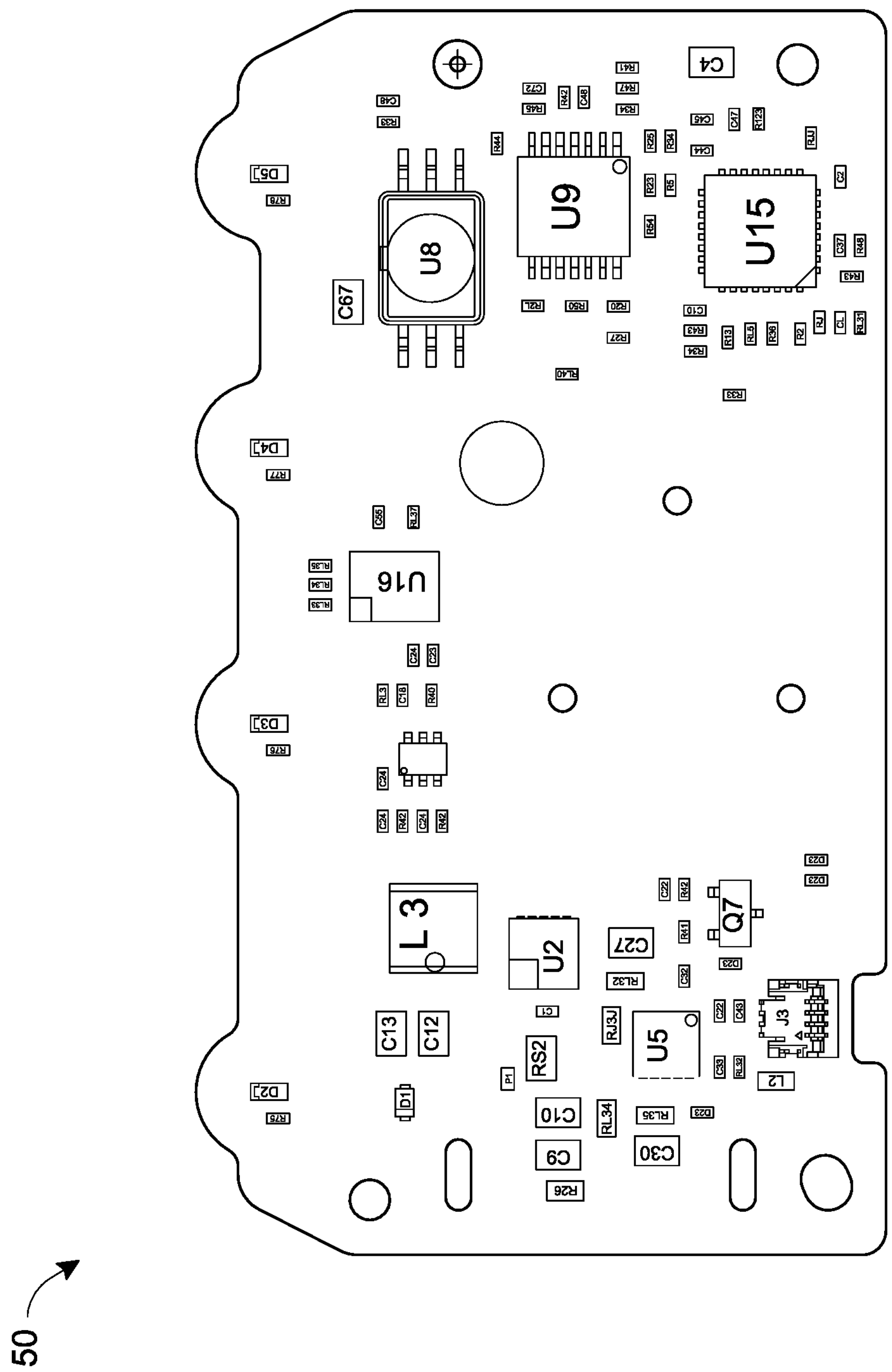
FIG. 23 illustrates art film of a top side assembly of a circuit board, such as the circuit board of FIGS. 20A and 20B.

FIG. 22A illustrates an example solder mask for a top side 40A of the PCBA 10, and FIG. 22B illustrates an example solder mask for a bottom side 40B of the PCBA 10. The first layer 30A, the second layer 30B, the third layer 30C, the fourth layer 300, the top side 40A, and the bottom side 40B may better illustrate certain features of the PCBA 10, including the multiple vias. The PCBA 10 can, for instance, have dimensions of around 57 mm by around 32 mm. The first layer 30A, the second layer 30B, the third layer 30C, and the fourth layer 30D can at least partly be composed of copper in some implementations. FIG. 23 illustrates example art film of a top side assembly 50 of the PCBA 10.

Figure 24:
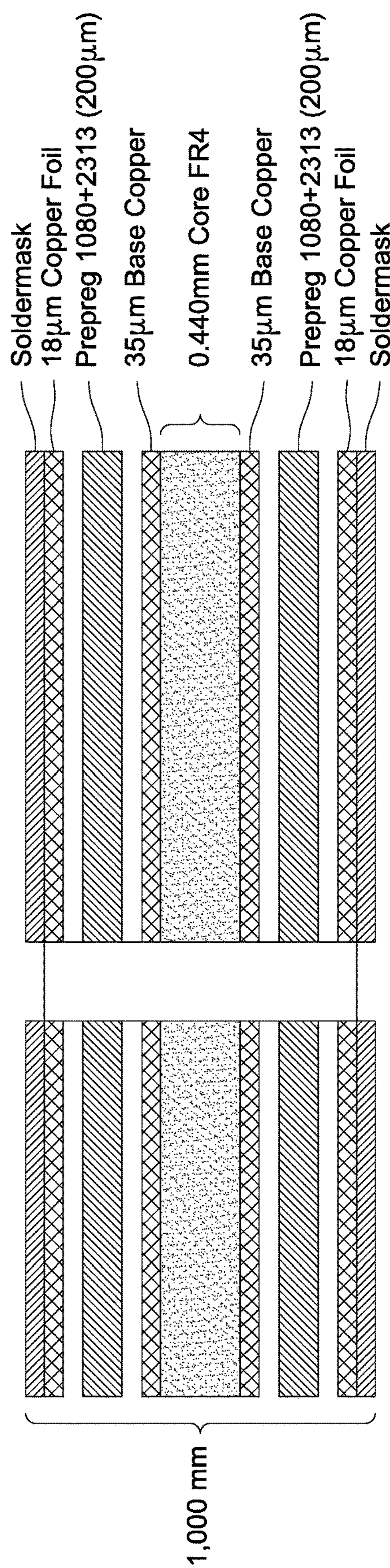
FIG. 24 illustrates layer constructions of a circuit board, such as the circuit board of FIGS. 20A and 20B.

FIG. 24 illustrates example layer constructions of the PCBA 10. The example layers construction can include the following features: The minimum conductor thickness outer layers after processing can be around 0.0334 mm. The minimum conductor thickness inner layers after processing can be around 0.0249. The finished board thickness overall can be around 1 mm. The solder resist thickness can be around 0.01 mm. The insulation coating can have a breakdown voltage of around 500 VDC. The solder resist type can be LPI on one or both sides. The surface finishing can be ENIG (Electroless Ni/Au [Ni 2.54 um MIN-Au 0.05 um MIN]).

In one implementation of the PCBA 10, its dimensions of the etched elements, vias, and insulations can be as follows: The logic track can be around 0.15 mm. The minimum insulation can be around 0.15 mm. The vias can be around 0.2 mm or 0.6 mm in diameter and plated. The PCBA 10 can include around 245 vias. The logic track tolerance can be around 0.0254 mm or 0.04 mm. The via tolerance can be around 0.076 mm. The plated hole tolerance can be around 0.076 mm. The non-plated hole tolerance can be around 0.05 mm. The plated slot tolerance can be around 0.127 mm. The non-plated slot tolerance can be around 0.1 mm.

The pump system can include a PCBA, such as the PCBA 10, positioned so that there is a gap between the edges of the PCBA and a housing, such as a plastic housing, of the pump system. Additionally or alternatively, the pump system can include a PCBA constructed so that components (such as one or more microcontrollers or memory devices) coupled to the PCB are more than a threshold distance (for example, around 0.5 mm, 1 mm, 2 mm, 3 mm, 4 mm, or 5 mm) from a perimeter of the PCB, such as shown in FIG. 23.

The pump system can include a PCBA, such as the PCBA 10, that has a track (for example, a grounding track) around a perimeter of a contact for a button. The button can be partly or entirely an elastomer. The button, while potentially being a partial isolator, may present an air gap via which a current may be conducted under certain circumstances. The track can be used to short an electrical discharge through the button and thus increase immunity of the pump system to electrical discharges.

The pump system can include a PCBA, such as the PCBA 10, that has a track (for example, a grounding track) around one or more holes in the PCBA, such as where the PCBA may be fastened to a housing of the pump system. In some implementations, the PCBA can include four holes where two holes may be used to screw the PCBA in place and the other holes may be for guidance rather than mounting. The mounting structures positioned in the holes used for guidance can have a sufficiently high breakdown voltage that no track may be included on the PCBA. Where conductive screws may be used, a breakdown voltage for the holes can be reduced (for instance, due to a shorter distance to a highly conductive path) and thus may benefit from a track.

The pump system can include a software input-output bus that is configured to be cognizant, including with respect to analog inputs. The pump system can include an EMI shield on top of one or more components such as a microcontroller or memory.

The pump system can include one or more nylon screws rather than metal screens to provide additional ESD protection for the pump system. A nylon screw can, for example, be used under a filter of the pump system.

The pump system can include one or more internal gaskets to provide additional ESD protection for the pump system. The pump system may also include no exposed metal or a minimal amount of exposed metal by covering metal parts, which may help prevent arcing. For instance, a plug for a charging cable can be electrically isolated from other components of the pump system and ears for connecting a clamp the pump system can be electrically isolated from other components of the pump system.

The pump system can include a capacitor electrically coupled to one or more individual connectors (for example, a USB connector or an antenna connector) and an ESD clamp. The pump system can include conformal coating, relatively short cable assemblies, relatively short layout traces, or encapsulate specific layout traces between planes. The pump system can also include planes and traces from a perimeter of a PCB, such as the PCBA 10, or grounded metal shielding.

The pump system can include no gap or change of material which could be an electrical channel to a PCBA, such as the PCBA 10, at energy and current levels experienced under defibrillation conditions. One or more light-emitting diodes (LEDs) of the pump system can be behind a solid, unbroken, translucent, front cover rather than having a light-pipe, lens, or other means to transmit the light.

In view of the device structures described herein, the pump system may not protect against overvacuum in the event of an electrical short because the pump system may have alternative capabilities to handle the electrical short.

The pump system can include electrical isolation to isolate water, urine, or blood ingress from short circuiting the pump system.

The pump system can, in some instances, use a tuned receiver for communication and perform shorting and capacitor protection of the receiver. Interference outside of a frequency of interest can be shorted to ground. The pump system may still have some vulnerability at the frequency of interest, but the vulnerability may notably be acceptable if the frequency is different from the spectrum of interference.

Features of the pump system to protect against electrical discharge can desirably further protect the pump system from damage or malfunction or protect a patient or clinician from being shocked.

Figure 25:
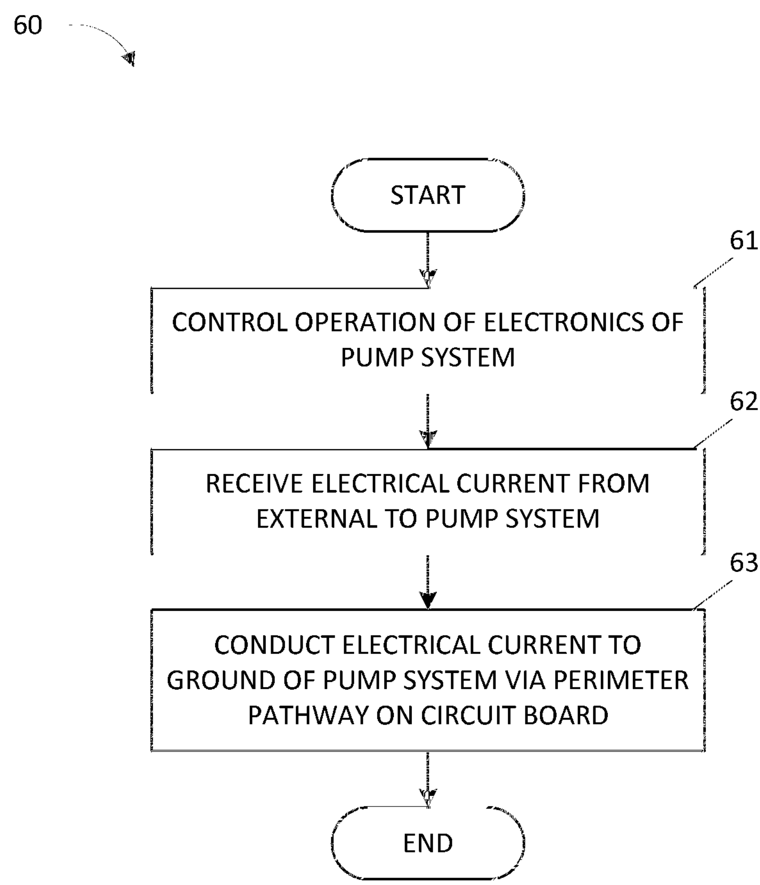
FIG. 25 illustrates a method for protecting a pump system from electrical discharge according to some embodiments.

FIG. 25 illustrates a method 60 for protecting a pump system from electrical discharge according to some embodiments. The method 60 can be performed by a pump system, such as the pump systems 100, 1000, 1100, or 1200, that includes a circuit board, such as the PCBA 10. For convenience, the method 60 is explained in the context of the pump systems described herein, but may instead be implemented in other systems not shown. The method 60 can advantageously, in certain embodiments, enable a pump system to be protected from electrical discharge that would traditionally have damaged the pump system.

At block 61, the method 60 can control operation of electronics of the pump system. For example, one or more controllers of the pump system like the controllers 1114 and 1202 or other components of the pump system control the electronics to perform various functions, such as activating or deactivating supply of negative pressure, detecting operating conditions such as leaks or blockages when supplying negative pressure, alarming based on operating conditions, or transmitting or receiving data from other electronics devices or users. The one or more controllers or other components can be mounted on a circuit board (such as, the PCBA 10) that has a conductive pathway (such, the conductive pathway 11 or 21) electrically coupled to an electrical ground for the circuit board. The circuit board can be positioned inside a housing of the pump system.

At block 62, the method 60 can receive an electrical current from external to the pump system. For example, the pump system can receive an electrical discharge from external to the housing of the pump system, such as via a user interface (such as, a button) or a fastener (such as, a screw) used to stabilize the structure of the housing.

At block 63, the method 60 can conduct the electrical current to ground of the pump system via a perimeter pathway on the circuit board. For example, the perimeter pathway can be a conductive pathway that extends around all or part (for instance, 20%, 25%, 30%, 35%, 40%, 45%, 50%, 55%, 60%, 65%, 70%, 75%, 80%, 85%, 90%, or 95% of a length) of a perimeter of a side of the circuit board or a perimeter of one or more elements on or holes in the circuit board. Examples of the perimeter pathway can include the conductive pathway 11 or 12 or the portions 13A, 13B, and 13C. The perimeter pathway can desirably thus be used to dissipate the electrical current without damaging the one or more controllers or other components can be mounted on the circuit board.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as “can,” “could,” “might,” or “may,” unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed:

1. An apparatus for applying negative pressure to a wound, the apparatus comprising:

a housing;

a negative pressure source configured to provide negative pressure via a fluid flow path to a wound covered by a wound dressing;

a printed circuit board supported by the housing and comprising a first conductive pathway extending around at least part of a perimeter of a first side of the printed circuit board, the first conductive pathway being electrically coupled to an electrical ground for the printed circuit board; and one or more components mounted on the printed circuit board, the one or more components being configured to activate and deactivate the negative pressure source, wherein the first conductive pathway comprises a track and is configured to protect at least some of the one or more components against an electrostatic discharge.

2. The apparatus of claim 1, wherein the printed circuit board comprises a second conductive pathway extending around at least part of a perimeter of a second side of the printed circuit board opposite the first side.

3. The apparatus of claim 2, further comprising a plurality of vias electrically connecting the first conductive pathway and the second conductive pathway through the printed circuit board.

4. The apparatus of claim 3, wherein the first conductive pathway extends around at least half of the perimeter of the first side, and the second conductive pathway extends around at least half of the perimeter of the second side.

5. The apparatus of claim 4, wherein the first conductive pathway extends around at least 75% of the perimeter of the first side, and the second conductive pathway extends around at least 75% of the perimeter of the second side.

6. The apparatus of claim 1, wherein the printed circuit board comprises at least four layers.

7. The apparatus of claim 1, wherein the printed circuit board comprises a second conductive pathway extending around at least part of an element on the first side of the printed circuit board, the second conductive pathway being electrically coupled to the electrical ground.

8. The apparatus of claim 7, wherein the element is a contact of a user interface component.

9. The apparatus of claim 7, wherein the second conductive pathway extends around at least part of a hole through the printed circuit board.

10. The apparatus of claim 7, wherein the second conductive pathway is electrically coupled to a third conductive pathway that extends between the printed circuit board and an outer surface of the housing.

11. The apparatus of claim 1, wherein the one or more components is configured to continue to activate and deactivate the negative pressure source subsequent to the wound dressing being exposed to a defibrillation shock while the negative pressure source is maintaining negative pressure below a negative pressure threshold.

12. The apparatus of claim 1, wherein the one or more components is further configured to output an alarm indicating presence of a leak in the fluid flow path or that pressure in the fluid flow path failed to satisfy a desired pressure threshold, the one or more components being further configured to not erroneously output the alarm as a result of the wound dressing being exposed to a defibrillation shock while the negative pressure source is maintaining negative pressure below a negative pressure threshold.

13. The apparatus of claim 1, wherein the one or more components is further configured to transmit first data to an electronic device or receive second data from the electronic device.

14. The apparatus of claim 1, wherein the negative pressure source is configured to perform negative pressure therapy when a magnitude of negative pressure under the wound dressing is maintained below a negative pressure threshold.

15. A method for operating a negative pressure wound therapy apparatus, the method comprising:

using one or more components of the negative pressure wound therapy apparatus, activating and deactivating supply of negative pressure via a fluid flow path to a wound dressing, the one or more components mounted on a printed circuit board supported by a housing of the negative pressure wound therapy apparatus, the printed circuit board comprising a first conductive pathway extending around at least part of a perimeter of a first side of the printed circuit board, the first conductive pathway comprising a track and being electrically coupled to an electrical ground for the printed circuit board; and conducting an electrostatic discharge from a source external to the negative pressure wound therapy apparatus to the electrical ground via the first conductive pathway to protect at least some of the one or more components from the electrostatic discharge.

16. The method of claim 15, wherein the first conductive pathway extends around at least half of the perimeter of the first side.

17. The method of claim 15, wherein the printed circuit board comprises a second conductive pathway extending around at least part of an element on the first side of the printed circuit board, the second conductive pathway being electrically coupled to the electrical ground; and further comprising conducting another electrostatic discharge from the source external to the negative pressure wound therapy apparatus to the electrical ground via the second conductive pathway to protect at least some of the one or more components from the another electrostatic discharge.

18. The method of claim 17, wherein the element is a contact of a user interface component.

19. The method of claim 15, further comprising transmitting first data to an electronic device or receiving second data from the electronic device using the one or more components.

20. The method of claim 15, wherein the printed circuit board comprises at least four layers.

* * * * *